(12) United States Patent
Boyd et al.

(10) Patent No.: US 9,042,987 B2
(45) Date of Patent: *May 26, 2015

(54) COMPRESSIBLE DEVICE

(71) Applicant: FEMEDA LTD, Middlesborough (GB)

(72) Inventors: Graham Peter Boyd, Chester (GB); Ian Gregson, Wigan (GB); Julia Heather Herbert, Manchester (GB); Edward Michael French, Holmfirth (GB)

(73) Assignee: Femeda Limited, Middlesborough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,825

(22) Filed: Aug. 12, 2013

(65) Prior Publication Data

US 2014/0200646 A1    Jul. 17, 2014

Related U.S. Application Data

(63) Continuation of application No. 12/094,953, filed as application No. PCT/EP2006/011286 on Nov. 24, 2006, now Pat. No. 8,509,900.

(30) Foreign Application Priority Data

Nov. 24, 2005  (GB) .................................. 0523917.3

(51) Int. Cl.
*A61N 1/32*    (2006.01)
*A61N 1/05*    (2006.01)
*A61N 1/36*    (2006.01)

(52) U.S. Cl.
CPC ............ *A61N 1/0524* (2013.01); *A61N 1/0512* (2013.01); *A61N 1/36007* (2013.01)

(58) Field of Classification Search
CPC  A61N 1/36007; A61N 1/0512; A61N 1/0524

USPC ............ 607/41, 115–116, 138, 148; 600/373
See application file for complete search history.

(56) References Cited

U.S. PATENT DOCUMENTS

| | | |
|---|---|---|
| 3,640,284 A | 2/1972 | Langis |
| 3,650,275 A | 3/1972 | Von Der Mozel |
| 3,800,800 A | 4/1974 | Garbe et al. |

(Continued)

FOREIGN PATENT DOCUMENTS

| | | |
|---|---|---|
| DE | 3518317 | 11/1986 |
| DE | 3827232 | 11/1989 |

(Continued)

OTHER PUBLICATIONS

International Search Report issued in corresponding PCT International Application No. PCT/EP20006/011286.

(Continued)

*Primary Examiner* — Rex R Holmes
(74) *Attorney, Agent, or Firm* — Knobbe Martens Olson & Bear, LLP

(57) ABSTRACT

An electro-stimulation device for the treatment of anterior and posterior pelvic floor muscle dysfunction is reversibly compressible and is fully self-contained. The device requires no external power sources or control and may be inserted into the vagina or anus through the use of an applicator. In the compressed state the device may be of tampon proportions and after use may easily be removed. The device utilizes a compressible electrode component.

20 Claims, 11 Drawing Sheets

(56) References Cited

U.S. PATENT DOCUMENTS

| | | | |
|---|---|---|---|
| 3,933,147 | A | 1/1976 | Du Vall et al. |
| 3,943,938 | A | 3/1976 | Wexler et al. |
| 3,973,571 | A | 8/1976 | Suhel |
| 4,106,511 | A | 8/1978 | Erlandsson |
| 4,515,167 | A | 5/1985 | Hochman |
| 4,580,578 | A | 4/1986 | Barsom |
| 4,688,575 | A | 8/1987 | DuVall |
| 4,785,828 | A * | 11/1988 | Maurer ............ 607/41 |
| 4,873,996 | A | 10/1989 | Maurer |
| 4,881,526 | A | 11/1989 | Johnson et al. |
| 4,909,263 | A | 3/1990 | Norris |
| 4,911,149 | A | 3/1990 | Borodulin et al. |
| 5,045,079 | A | 9/1991 | West |
| 5,046,511 | A | 9/1991 | Maurer et al. |
| 5,063,929 | A | 11/1991 | Bartelt et al. |
| 5,117,840 | A | 6/1992 | Brenman et al. |
| 5,199,443 | A | 4/1993 | Maurer et al. |
| 5,314,465 | A | 5/1994 | Maurer et al. |
| 5,370,671 | A | 12/1994 | Maurer et al. |
| 5,376,206 | A | 12/1994 | Maurer et al. |
| 5,385,577 | A | 1/1995 | Maurer et al. |
| 5,456,709 | A | 10/1995 | Hamedi |
| 5,516,396 | A | 5/1996 | Maurer et al. |
| 5,562,717 | A * | 10/1996 | Tippey et al. .......... 607/41 |
| 5,571,118 | A | 11/1996 | Boutos |
| 5,618,256 | A | 4/1997 | Reimer |
| 5,662,699 | A | 9/1997 | Hamedi et al. |
| 5,667,615 | A | 9/1997 | Maurer et al. |
| 5,702,428 | A | 12/1997 | Tippey et al. |
| 5,759,471 | A | 6/1998 | Malewicz |
| 5,800,501 | A * | 9/1998 | Sherlock .......... 607/138 |
| 5,800,502 | A | 9/1998 | Boutos |
| 5,816,248 | A | 10/1998 | Anderson et al. |
| 5,871,533 | A | 2/1999 | Boutos |
| 5,875,778 | A | 3/1999 | Vroegop |
| 5,881,731 | A | 3/1999 | Remes |
| 5,921,944 | A | 7/1999 | Borodulin et al. |
| 6,063,045 | A | 5/2000 | Wax et al. |
| 6,086,549 | A | 7/2000 | Neese et al. |
| 6,185,465 | B1 * | 2/2001 | Mo et al. .......... 607/138 |
| 6,240,315 | B1 | 5/2001 | Mo et al. |
| 6,264,582 | B1 | 7/2001 | Remes |
| 6,289,245 | B1 | 9/2001 | Mo et al. |
| 6,321,116 | B1 | 11/2001 | Mo et al. |
| 6,432,037 | B1 | 8/2002 | Eini et al. |
| 6,470,219 | B1 | 10/2002 | Edwards et al. |
| 6,631,297 | B1 | 10/2003 | Mo |
| 6,865,423 | B2 | 3/2005 | Oldham |
| 8,509,900 | B2 * | 8/2013 | Boyd et al. .......... 607/41 |
| 2002/0000233 | A1 | 1/2002 | Jude |
| 2002/0068900 | A1 | 6/2002 | Barnes |
| 2003/0004553 | A1 | 1/2003 | Grill |
| 2003/0083590 | A1 | 5/2003 | Hochman et al. |
| 2003/0087734 | A1 | 5/2003 | Kring |
| 2003/0135245 | A1 | 7/2003 | Campos |
| 2003/0220589 | A1 | 11/2003 | Leivseth et al. |
| 2004/0030360 | A1 | 2/2004 | Eini et al. |
| 2004/0054392 | A1 | 3/2004 | Dijkman |
| 2004/0122341 | A1 | 6/2004 | Walsh |
| 2004/0236385 | A1 | 11/2004 | Rowe |
| 2005/0228316 | A1 | 10/2005 | Morgenstern |

FOREIGN PATENT DOCUMENTS

| | | |
|---|---|---|
| DE | 3919453 | 12/1989 |
| DE | 4035267 | 5/1991 |
| DE | 4022074 | 2/1992 |
| DE | 4436634 | 4/1996 |
| DE | 19715870 | 10/1998 |
| DE | 19755243 | 6/1999 |
| DE | 10162484 | 7/2003 |
| EP | 0088173 | 9/1983 |
| EP | 178514 | 4/1986 |
| EP | 0263466 | 4/1988 |
| EP | 0411632 | 2/1991 |
| EP | 473131 | 3/1992 |
| EP | 638329 | 2/1995 |
| EP | 1279413 | 1/2003 |
| EP | 1704892 | 9/2006 |
| FR | 2547203 | 12/1984 |
| FR | 2655271 | 6/1991 |
| FR | 2709252 | 3/1995 |
| FR | 2709422 | 3/1995 |
| FR | 2762983 | 5/1997 |
| FR | 2754717 | 4/1998 |
| FR | 2757070 | 6/1998 |
| FR | 2767481 | 2/1999 |
| FR | 2806634 | 9/2001 |
| FR | 2827520 | 1/2003 |
| GB | 1480103 | 7/1977 |
| GB | 1599466 | 10/1981 |
| GB | 2 404 339 | 2/2005 |
| JP | 61-103149 U | 7/1986 |
| JP | 9122248 | 5/1997 |
| JP | 11019223 | 1/1999 |
| JP | 2006167385 | 6/2006 |
| NL | 8902023 | 8/1989 |
| WO | WO 8401515 | 4/1984 |
| WO | WO 84/03211 | 12/1984 |
| WO | WO 9214510 | 9/1992 |
| WO | WO 9324176 | 12/1993 |
| WO | WO 9731679 | 9/1997 |
| WO | WO 97/47357 | 12/1997 |
| WO | WO 9748446 | 12/1997 |
| WO | WO 98/34677 | 8/1998 |
| WO | WO 9935986 | 7/1999 |
| WO | WO 0006246 | 2/2000 |
| WO | WO 0062699 | 10/2000 |
| WO | WO 01/60446 | 8/2001 |
| WO | WO 01/95829 | 12/2001 |
| WO | WO 0209805 | 2/2002 |
| WO | WO 03-007862 | 1/2003 |
| WO | WO 2005077276 | 8/2005 |

OTHER PUBLICATIONS

International Search Report issues in corresponding International Application No. PCT/EP2006/011288 on Apr. 27, 2007.

Ohlsson, et al., "Miniaturised Device for Long-Term Intravaginal Electrical Stimulation for the Treatment of Urinary Incontinence," Medical and Biological Engineering and Computing, col. 26, No. 5, Sep. 1, 1988, pp. 509-515.

International Search Report issued in corresponding international Application No. PCT/EP2006/011287 filed Nov. 24, 2006.

Jeyaseelan, S.MS et al., "An evaluation of a new pattern of electrical stimulation as a treatment for urinary stress incontinence: a randomized, double-blind, controlled trial", Clinical Rehabilitation, 2000, p. 631-640, 14, SAGE Publications.

* cited by examiner

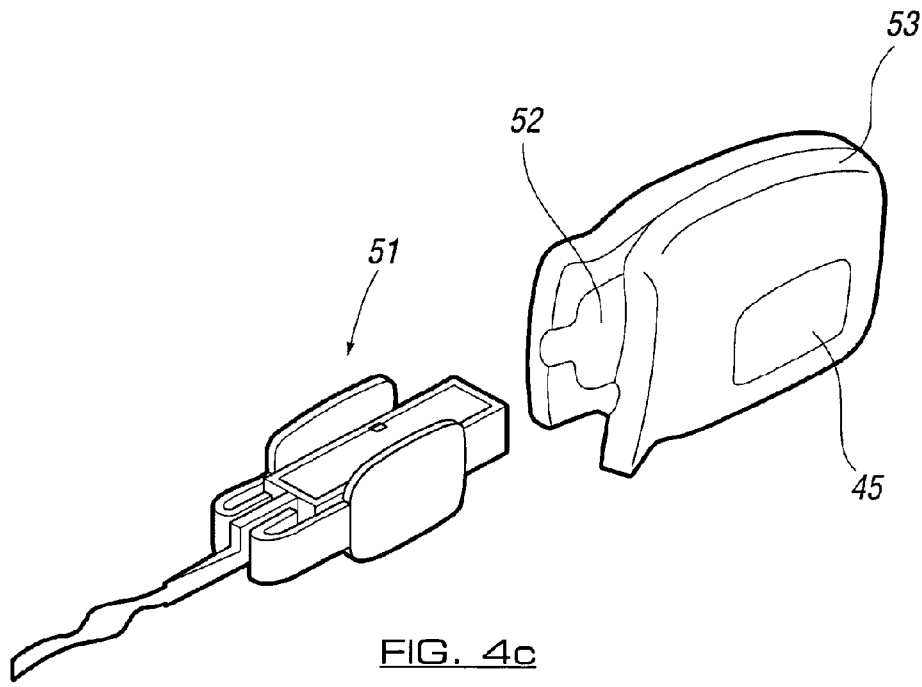
FIG. 4c
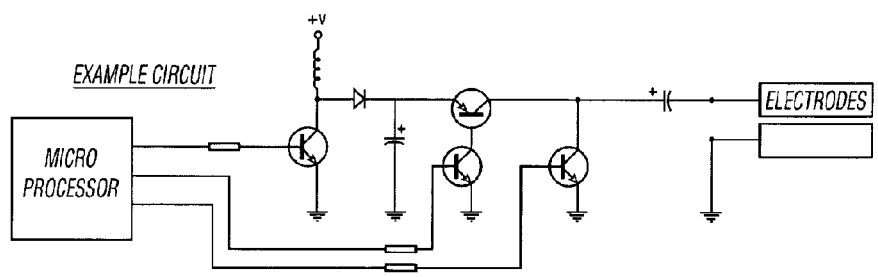
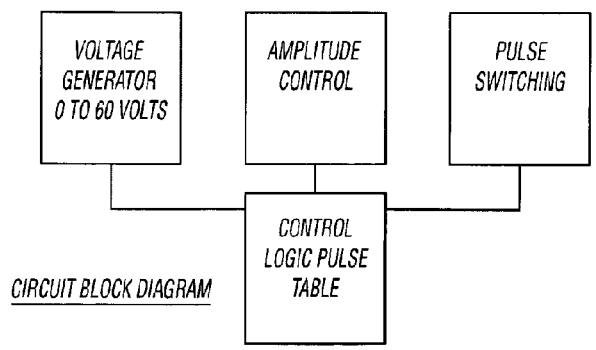
FIG. 5

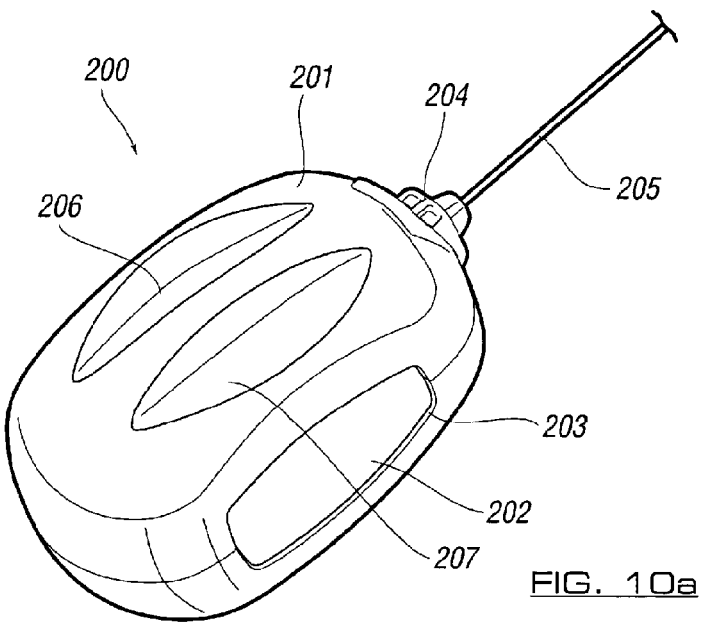
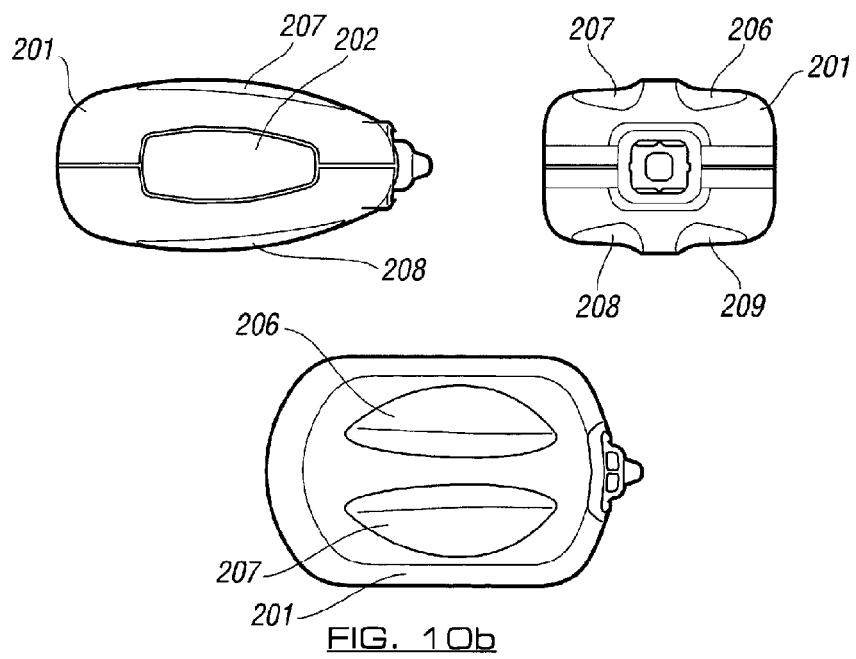

COMPRESSIBLE DEVICE

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present invention relates to electrical nerve and muscle stimulation and to electro-stimulation devices and methods for such electro-stimulation and in particular to electro-stimulation devices and methods for use in the electro-medical treatment and electro-stimulation of the muscle and nerve groups associated with pelvic floor musculature and especially although not exclusively where there is dysfunction with this musculature resulting in urinary and/or faecal incontinence.

2. Description of the Related Art

Caring for women with pelvic floor disorders has become an increasingly important component of women's healthcare. These disorders, which include urinary and faecal incontinence, sexual dysfunction as well as pelvic organ prolapse, affect a large segment of the adult female population. One common cause is trauma during vaginal delivery which may result in a variety of pelvic floor complaints; urinary stress and urge incontinence and faecal incontinence are the most frequent and long lasting.

In order to restore function of the pelvic floor muscles after childbirth, women have been encouraged to perform pelvic floor muscle exercises. Pelvic floor muscle exercises (PFME) are a known treatment for exercising muscles which control the urinary function. The theoretical basis of using pelvic floor muscle exercise for the treatment and prevention of stress urinary incontinence is based on the muscular changes that may occur after specific strength training. A strong and well-functioning pelvic floor can build a structural support for the bladder and the urethra. Postpartum pelvic floor muscle training has been demonstrated to be effective in the prevention and treatment of stress urinary incontinence in the immediate postpartum period. The results also showed that the success of postpartum pelvic floor muscle exercise depended on training frequency and intensity of effort.

Pelvic floor muscle exercises are also called Kegel exercises after Dr. Arnold Kegel, who in the late 1940's, promoted them to strengthen the pelvic floor muscles. The muscles involved in PFME strengthening are the Levator Ani, which include the pubococcygeus, pubovaginalis, puborectalis, iliococcygeus, and also the iliococcygeus muscles collectively these muscles are referred to as the "deep muscles" of the pelvic floor complex. These muscles contract and relax under patient's command allowing the storage and discharge at a socially acceptable time and place, of both urine and faeces. PFME will also activate the "superficial muscles", including ischiocavernosus, bulbospongiousus, the transverse peroneii and the urethral sphincters. Regular exercise is necessary to increase function. Muscle activation promotes function.

Such exercises require the relevant muscles to be contracted and relaxed regularly during the course of a day or over a period of many weeks, often months. A known aid for such exercises comprises a pre-formed core of rigid plastics material. Such aids are provided in a set of graded weights, requiring the (female) patient to insert them into the vagina, and retain them in position. However, this can be difficult for some women. The smallest available weight may be too heavy, or the size is incorrect. For many women the correct positioning of the device is problematic. These devices are not suitable for use by women with moderate or severe genitor-urinary prolapse . . . .

A variety of non-surgical approaches have been investigated as treatments of urinary incontinence, including PFME, biofeedback, other behavioral therapies, and pelvic floor stimulation. Pelvic floor stimulation (PFS) involves the electrical stimulation of pelvic floor muscles using a probe or skin electrodes wired to a device for controlling the electrical stimulation. It is thought that pelvic floor stimulation via the pudendal nerve and nerve to the Levator Ani will improve urethral closure by activating the pelvic floor musculature. In addition, PFS is thought to improve partially denervated urethral and pelvic floor musculature by enhancing the process of reinnervation. PFS is also thought to improve neuromuscular coordination for the patient enabling them to perform correct voluntary contractions in the future. Patients receiving PFS may undergo treatments in a physician's office or physical therapy facility, or patients may undergo initial training in a physician's office followed by home treatment with a rented or purchased pelvic floor stimulator.

Conventional electro-stimulation treatments for urinary and faecal incontinence require a patient to apply stimulation via an internal electrode or skin electrodes in electrical contact with the body. Electrical stimulation units for home or office use are programmed to deliver stimulation at pre-set frequencies. A conventional electro-stimulation system includes pulse generator housed in a portable battery box that is attached by an appropriate lead to an electrode.

The electro-stimulation systems conventionally use a drive signal to the electrode. Differing therapeutic effects are achieved using different drive signal types. Conventionally such stimulation systems allow for a variation of drive signal pulse width or frequency by the patient. However each such known portable stimulation system has electronics which are dedicated for providing a specific predetermined drive signal having a geometry and other characteristics matched to the intended therapeutic effect. Adjustment of the control signal is conventionally provided by electronic push switches and or rotational control knobs. Such switches and knobs can often be tampered with by the patient, and it is thus difficult for a medical practitioner prescribing electro-stimulation treatment to control the treatment when the patient is away from a clinic.

Other known electro-stimulators include microprocessor based units, but these have a problem that conventionally, specialised pre-programming equipment needs to be used at the clinic to set the signal parameters. Such equipment is expensive and often difficult to use.

In EP 0411632 there is described an expandable vaginal electrode that is adapted to be inserted into a woman's vagina and which is utilized with a controller external to the device and woman's body.

In WO 98/34677 there is described a tampon especially for women suffering from urinary incontinence that is made of sponge like material and is used in the wet state. The tampon is used with a non-insulated electrode and external control source to treat incontinence.

In NL 8902023 there is described an electro-stimulator for combating incontinence. The stimulator is rigid and self-contained.

Whilst there are various devices in the art and available commercially for the treatment of urinary and/or faecal incontinence there is a continuing need for new devices that offer effective treatment through effective contact of electrodes with muscles to be treated, that are comfortable and easy to use and which afford the possibility for the patient to self treat without medical intervention and/or without the guidance of a physician.

SUMMARY OF THE INVENTION

The present invention and its specific embodiments aim to address the above identified needs and problems associated with conventional plug type electrodes and electro-stimulation devices and the problems encountered in the treatment of anterior and posterior pelvic floor muscle dysfunction including prolapse, difficult defecation, sexual dysfunction and incontinence using such electro-stimulation devices.

In accordance with the present invention there is provided a self-contained vaginal or anal electro-stimulation device for the neuromuscular electro-stimulation of the musculature of the pelvic floor complex, which device comprises a body being reversibly compressible in at least one dimension and at least two electro-conductive elements located at or on the external surface of the body, an internal power source and internal pre-programmed means for the generation and control of electrical pulses for the neuromuscular electro-stimulation of the musculature of the pelvic floor complex via the electro-conductive elements. Thus the device of the present invention is capable of the neuromuscular electro-stimulation of the musculature of the pelvic floor complex via the endovaginal (transvaginal) or endoanal (transanal) application and use of the device. In the following description reference will be made to the anal or vaginal endocavity. This refers to the location within the anus or vagina at which point the musculature of the pelvic floor complex may be stimulated by the device of the present invention.

By self-contained is meant that the electro-stimulation device does not need or use, an external power source, an external electrical pulse generator or an external control unit. Intervention or operation by a physician or other medical expert is not required. Each electro-stimulation device of the present invention contains all the essential elements that are required to deliver a single electro-stimulation treatment session for the treatment of anterior and posterior pelvic floor muscle dysfunction. Preferably the electro-stimulation device does not have any means for enabling the enclosed battery or batteries to be replaced or re-charged. Although not preferred it is possible to have the power source for the device external to the device and providing power through an electrical cord to the device. In a further embodiment the device may not contain an internal power source but receive sufficient power for the required treatment cycle through external means during or just prior to its deployment. There is no means provided for the re-programming of the internal microprocessor controlled circuitry e.g. control unit and/or signal generator to provide a different electro-stimulation regime as this is pre-programmed into the device. The electro-stimulation device is disposable after use and is designed to be a one-shot electro-stimulation device, meaning that it is used for a single session of therapy and is then discarded.

The body of the electro-stimulation device is compressible in at least one dimension. The dimensions of the electro-stimulation device in its non-compressed form are such that one or more of its external surfaces and the electro-conductive elements at or on the surface of the electro-stimulation device body will be in contact with one or more surfaces of the vaginal or anal endocavity. The device in-situ will typically be in a partially compressed state. This state being induced by contact of the device with the surfaces of the endocavity. In this state one or more of the external surfaces of the electro-stimulation device and the electro-conductive elements at or on the surface of the electro-stimulation device body are in intimate contact with one or more surfaces of the endocavity. They are forced into contact with the endocavity surfaces by the resilient force induced by the materials used to manufacture the device body and/or due to the internal structure of the device. Normally, an electro-stimulation device of these dimensions could not easily be inserted into the vagina or anus for use. However as the electro-stimulation device of the present invention is reversibly compressible the dimensions of the electro-stimulation device may be reduced to the required dimensions for easy insertion. The extent of compressibility is such that the device may be compressed to a size such that it may be easily inserted into the vaginal or anal endocavity Preferably, the dimensions of the body of the electro-stimulation device, the choice of material for the manufacture of the body of the electro-stimulation device and/or the structure of the body of the electro-stimulation device are such that when the electro-stimulation device is in-situ the surface of the electro-stimulation device body and the electro-conductive elements at or on the surface of the electro-stimulation device body are forced e.g. under pressure, against one or more surfaces of the endocavity. Preferably the electro-stimulation device body is manufactured from one or more resiliently deformable materials. Thus the body of the electro-stimulation device being resiliently deformable for insertion is, after insertion and in-situ, able to expand in order to conform to the shape of vaginal or anal endocavity. In-situ the electro-stimulation device is able to change its shape to substantially conform to change in the shape of the endocavity during use of the device and so the device is conformable during use. It should be understood that the dimensions described in detail below are for devices designed for use in the vaginal endocavity. Devices suitable for use in the anal endocavity will be of smaller dimensions due to the smaller size of that endocavity compared to that of the vagina.

In a further embodiment the electro-stimulation device body may be compressible due to a combination of the choice of materials used for its manufacture and due to its structure. For example the electro-stimulation device body may be manufactured from resiliently deformable material and the interior of the electro-stimulation device body may be hollow. In this embodiment when the electro-stimulation device is compressed the body material is deformed and the hollow interior may be constricted or collapsed to a smaller volume. This combination may provide for an electro-stimulation device with a high magnitude of reversible compressibility so that the electro-stimulation device may be compressed to a significantly smaller volume compared to the non-compressed state.

The material used for the electro-stimulation device body is preferably a resiliently deformable/compressible biocompatible material and may be formed as a solid or semi-solid mass of a resiliently compressible biocompatible material that allows the electro-stimulation device body to resiliently deform and to conform to the shape of the object deforming the device e.g. the anal or vaginal endocavity or, when used, by the wall of an applicator. The resiliently deformable/compressible biocompatible materials may be selected or tailored to provide any desired degree of deformability/compressibility and/or resilient properties. The material can be selected and adjusted to provide the desired attributes of softness, and/or firmness and is selected in relationship with the desired level of support required for effective contact with the endocavity walls whilst maintaining an ability to conform to the shape of the anal or vaginal walls. It is preferred that the deformable/compressible device body comprises biocompatible material in the form of compressible/deformable foam. Examples of suitable materials include thermoplastic elastomeric foam materials such as polyvinyl formal foam (PVF), polyurethane foams. In one preferred embodiment the device body is prepared from polyurethane and most preferably from moulded polyurethane foam. These polyurethane foams may be prepared from polyols and isocyanates, which are mixed and injected into a moulding tool where they foam and cure. In one alternative embodiment the device body is provided by two moulded halves which are formed from a suitable polymer and then brought together to encapsulate the other components of the device; the two halves may for example be sealed together by hot plate welding to provide a hollow device body. In this embodiment the device body does not contain foam.

The foamed device body may comprise a closed cell or open cell foam. It is preferred that the foam is open celled. The use of open celled foams is desirable as it provides for good levels of compressibility and deformability. In a preferred embodiment the foam formulation is selected to be self skinning. During manufacture of the device body, by injection of a foamable composition into a suitable mold, a skin of material compositionally identical to the composition of the foam of the interior of the body is formed at the surface of the device body. It is preferred that the foam of the device body has a relatively low density. This ensures maximum compressibility/deformability for ease of insertion into the applicator if used and for insertion into the relevant body endocavity. It is preferred that the foam density is less than 250 $Kgm^{-3}$ preferably less than 200 $Kgm^{-3}$ and most preferably less than 150 $Kgm^{-3}$. It is preferred that the foam density is within the range of from 250 to 80 $Kgm^{-3}$, more preferably within the range from 200 to 80 $Kgm^{-3}$, more preferably within the range from 200 to 100 $Kgm^{-3}$ and most preferably within the range from 150 to 100 $Kgm^{-3}$. In addition to relatively low density it is also preferred that the polymer system used in the manufacture of the foam does not produce a hard foam material, which is strongly resistant to deformation. The polymer system is preferably selected to produce a relatively soft foam material that has relatively low values for IDF (indentation force deflection as measured according to ASTM D 3574). At the same time the materials for manufacture of the device body foam should be selected to produce a device body foam that is strong enough so that the skinned surface and the bulk of the foam remains intact during manufacture and use of the device.

As the devices of the present invention may be stored in the compressed state e.g. within an applicator, for extended periods of time the materials used in its manufacture must be stable and retain their properties for the normal shelf-life of the device. In particular the resiliently deformable/compressible materials must retain their resilient properties during storage so that when released from compression e.g. when expelled from an applicator they are able to expand to the normal non-compressed state and to exert the required pressure against the anal or vaginal endocavity. It is also important that the materials used do not leach chemicals e.g. plasticizers etc during storage. The resiliently deformable/compressible material used to prepare the device body should exhibit relatively rapid change from the compressed to the non-compressed state, so that on insertion the device rapidly expands from the compressed state to make contact with the relevant endocavity. This change from compressed to non-compressed state should ideally occur in a matter of seconds, preferably less than 10 seconds, more preferably less than 5 seconds and most preferably less than 3 seconds.

The electro-stimulation device of the present invention may comprise an electro-stimulation device body that has been moulded around the interior components of the electro-stimulation device to encapsulate them. Alternatively the electro-stimulation device body may be manufactured with a hollow interior into which the interior components may be placed during manufacture of the electro-stimulation device. In a further embodiment the device body may be moulded in two halves preferably by over moulding each of the electro-conductive elements; the two halves are then sealed around internal components using such techniques as hot plate welding. The device may be manufactured by a combination of any of these methods. It is preferred however that the device body is pre-moulded in one piece with cavities, accessible from the exterior, which are capable of receiving and accommodating the electro-conductive elements and an electronic sub-assembly. In a preferred embodiment the moulded device body comprises a cavity for an electronic sub-assembly accessible from the distal end of the moulded device body and preferably moulded recesses along each side of the device body to accommodate electro-conductive elements on each side of the device.

In a further embodiment the electro-stimulation device of the present invention may have and preferably does have a defined shape. In particular the shape of the electro-stimulation device may be selected to exhibit certain properties in relation to its symmetry. It is preferred that a cross-sectional shape of the device, perpendicular to the axis of insertion and when viewed along the axis of insertion, is non-circular. Preferably, the perpendicular cross-section is taken at the mid-point of the device along the axis of insertion. Preferably, the shape of the electro-stimulation device is such that the shape of any cross-section perpendicular to the axis of insertion is such that the electro-stimulation device may not be freely rotated about the axis of insertion when in-situ, whilst at the same time providing the maximum potential contact of the electro-stimulation device with the walls of the anal or vaginal endocavity. In one embodiment this perpendicular cross-sectional shape may exhibit no planes of reflective symmetry or axis of rotational symmetry e.g. the shape is completely asymmetrical. In one embodiment, whilst being non-circular in cross-section, it is preferred that the perpendicular cross-sectional shape exhibits at least one reflective axis and/or rotational axis of symmetry but not infinite reflective axis or rotational axis of symmetry; thus the perpendicular cross-sectional-shape may be any non-circular shape. In a preferred embodiment the perpendicular cross-sectional shape approximates to a rectangle or square, which preferably has softened rounded corners being corners that are not angular and do not define a right angle or any defined angle. The extent of rounding of these corners is such that on viewing the device in perpendicular cross-section along the axis of insertion it is clear that the perpendicular cross-sectional shape is derived from a broadly rectangular or square shape. Preferably the perpendicular cross-sectional shape is broadly square or rectangular in shape. Preferably the perpendicular cross-sectional shape exhibits at least one axis of reflective symmetry and more preferably at least two axis of reflective symmetry. In the broadly square shaped or rectangular shaped embodiments the perpendicular cross-sectional shape exhibits at least two axis of reflective symmetry and at least one axis of rotational symmetry; the broadly square shaped embodiment having four reflective and one rotational axis of symmetry and the broadly rectangular shaped embodiment having two reflective and one rotational axis of symmetry. The device of the present invention may have a shape, such that when the device is viewed from the side, that is in profile along the axis of insertion of the device, the shape of the side is broadly similar to the shape of the device when viewed along the axis of insertion e.g. from the front of the device. The device, when viewed from above, at approximately 90 degrees to the side view, may exhibit a shape which is of similar or different shape and dimensions to those of the side or front views. In a preferred embodiment the side and top views are of different shape and or dimensions from that of each other and the front view of the device. In one embodiment the side view may exhibit no rotational or reflective axis of symmetry. In one embodiment, the side view may exhibit one rotational and two reflective axis of symmetry; in a preferred embodiment, it exhibits one reflective and no rotational axis of symmetry. In a further embodiment the top view may exhibit no rotational or reflective axis of symmetry. In a further embodiment the top view may exhibit a single rotational and two reflective axis of symmetry; in a preferred embodiment it exhibits one reflective and no rotational axis of symmetry. The device may have two distinct ends. The first is proximate to the point of insertion into the anus or vagina and the second is remote from the proximate end or point of insertion. In one embodiment the proximate end is larger in dimensions compared to the remote end of the device; the device will therefore have a tapered or pear shaped appearance when viewed from either the side or top of the device or from both perspectives. It is preferred that dimensions of such a device are greater when viewed from the top compared to those when viewed from the side of the device so that the device may have a slightly flattened appearance when orientated for insertion. Alternatively the dimensions may be reversed with the proximate end having smaller dimensions than the remote end of the device.

In one embodiment the dimensions of the electro-stimulation device body are greater along the axis of insertion compared to the dimensions perpendicular e.g. in cross-section to that axis. In an alternative embodiment the dimensions of the body may be similar in both views.

The compressibility of the device is such that it may easily be inserted into the relevant endocavity. The limits of compressibility will be set by the nature of the materials used e.g. resiliently deformable material for the body, by the nature of the internal structure e.g. the presence of hollow cavities and also the dimensions of the electronic components used internally. Ideally these are selected to afford the maximum amount of compressibility for the device. In one embodiment the electro-stimulation device may be compressed to dimensions that are different in proportion relative to each other compared to the same dimensions in the non-compressed state. In a further embodiment the device may be compressible to the same or similar extent in all dimensions. In a further embodiment the device has greater compressibility in the plane perpendicular to the axis of insertion of the device. The electro-stimulation device may have two dimensions perpendicular to the axis of insertion that have different degrees of compressibility. For example in the non-compressed state the electro-stimulation device may have a length of approximately 60 to 65 mm and a height of approximately 30 to 45 mm and a width of approximately 30 to 45 mm. On compression the compressed electro-stimulation device may have a length of approximately 60 to 65 mm, a height of approximately 25 mm and a width of approximately 15 mm. In the non-compressed state the electro-stimulation device may have a length in the range of from approximately 30 to 120 mm, preferably approximately 40 to 100 mm, more preferably approximately 45 to 75 mm and most preferably approximately 45 to 65 mm. In the non-compressed state the electro-stimulation device may have at least two equal dimensions or at least two non-equal dimensions perpendicular to the axis of insertion that are within the range of approximately 30 to 60 mm, preferably approximately 35 to 55 mm and most preferably approximately 35 to 50 mm. Preferably the length of the electro-stimulation device in the non-compressed state is equal to the length of the electro-stimulation device in the compressed state. The materials selected for the manufacture of the electro-stimulation device and/or the structure of the electro-stimulation device are such that at least one of the dimensions of the electro-stimulation device perpendicular to the axis of insertion may be reduced on compression by at least 20%, more preferably at least 40%, more preferably at least 50% and most preferably at least 60%. All of the dimensions of the electro-stimulation device perpendicular to the axis of insertion may be reduced on compression by at least 15%, preferably at least 25%, more preferably at least 35% and most preferably by at least 40%. In the compressed state the dimensions of the electro-stimulation device perpendicular to the axis of insertion may be such that the width is in the range of 10 to 35 mm, preferably 10 to 30 mm, preferably 10 to 25 mm and most preferably 15 to 20 mm and the height of the compressed electro-stimulation device is within the range of 10 to 40 mm, preferably 10 to 35 mm, more preferably 10 to 30 mm and most preferably within the range of 15 to 30 mm. It is preferred that the device has sufficient compressibility such that the volume of the device in the compressed state is reduced by at least 20% compared to that in the non-compressed state, preferably it is reduced by at least 25%, more preferably it is reduced by at least 30%, more preferably it is reduced by at least 40%, more preferably it is reduced by at least 50%, and most preferable by at least 75%.

In a further embodiment the electro-stimulation device of the present invention may be made of materials and constructed in such a way that it may be compressed into a shape that approximates to a tampon form. In this form it is easier to insert into the vagina or anus. Once inserted and in place the electro-stimulation device in tampon form will expand and come into contact with the walls of the vaginal or anal endocavity.

Thus the electro-stimulation device of the present invention may be adapted for deployment into an anal or vaginal endocavity via the use of an applicator. The applicator may for example be a hollow tubular applicator containing the electro-stimulation device in its bore in the compressed state. The device is deployed from the applicator into the vagina or anus. Typically the applicator including compressed device is positioned at the vaginal introitus (opening) or anal sphincter and the device is then discharged from the applicator into the anus or vagina by operation of the plunger. Once inside the vagina or anus the compressed electro-stimulation device may expand.

The present invention also provides for a device for the electro-stimulation of the musculature of the pelvic floor complex e.g. for the treatment of anterior and posterior pelvic floor muscle dysfunction, which device comprises an electro-stimulation device according to the present invention in combination with an applicator. Preferably the applicator comprises an outer member and an inner member, the electro-stimulation device being located within the outer member.

In this embodiment the outer member is adapted to house the electro-stimulation device and the inner member. The inner member is located and movable within the bore of the outer member and co-operates with the outer member to force the discharge the electro-stimulation device from the bore of the outer member, after the applicator has been positioned at the vaginal introitus (opening) or anal sphincter.

In a preferred embodiment the inner member is adapted to assist with activation of the electro-stimulation device as it is deployed from the applicator. In this embodiment adaptation may take the form of a specific shape or arrangement of the proximate end of the inner member so that it comes into contact with part of the activation mechanism for the electro-stimulation device. During deployment of the electro-stimulation device from the applicator the inner member makes contact with and remains in contact with this activation mechanism until the device is deployed. It is the contact between the proximate end of the inner member and the activation mechanism coupled with a requisite amount of stiction between the electro-stimulation device and the outer member of the applicator that ensures that enough force is applied to the activation mechanism during deployment to activate the device. The force required to activate the activation mechanism through this contact is less than the force required to overcome the stiction between the outer member and enclosed electro-stimulation device. This means that the force applied to the inner member during deployment will activate the activation mechanism before the inner member through applied pressure forces the electro-stimulation device out of the outer member and into the endocavity. The preferred activation mechanism associated with use of the applicator will be described in more detail below. In a preferred embodiment the applicator comprises a detent position, which assists in preventing inadvertent activation of the electro-stimulation device during manufacture, storage or unpacking by the end user. A reasonable force must be applied to the inner member to disengage this detent and allow the inner member to move relevant to the outer member. In a further preferred embodiment the inner member is in the form of a hollow tube. This arrangement has the advantage that a withdrawal cord when used is able to pass down the bore of the tube and is thus protected from being trapped between the inner and outer members during deployment of the device. This arrangement also assists with alignment during assembly of the applicator incorporating the electro-stimulation device.

The applicator may be marked, indented or grooved in such a way that the orientation for insertion is obvious to the user.

Apart from the device body the electro-stimulation device comprises an electronic sub-assembly which comprises at least two electro-conductive elements and a complete set of internal electrical components required to generate and control electro-stimulating pulses, via the electro-conductive elements, to the musculature of the pelvic floor complex. In particular these components comprise a power source, a signal generating means and microprocessor based control circuitry. The circuit includes a voltage generator preferably having a voltage range of 0 to 60 volts, an amplitude control circuit, a control logic pulse table and a pulse switching circuit. It is preferred that the internal electrical components are located on a printed circuit board (PCB). In addition a means for activating the circuit electronics is associated with the internal electrical components.

The circuit inside the electro-stimulation device may contain one or more batteries as its power source. As the electro-stimulation device is single use device the battery may be a small battery that is easily accommodated within the compressed dimensions of the electro-stimulation device. Suitable batteries include batteries that have low levels of potential harmful materials such as low or zero mercury zinc anode batteries or lithium manganese button cells. The device may be charged or powered from an external source but it is preferred that one or more internal batteries are the exclusive source of power for the device.

The electro-conductive elements may be provided upon and attached to the surface of the electro-stimulation device and connected to the interior circuitry via appropriate conductive paths e.g. wiring. Alternatively, the electro-conductive elements may be formed as part of the interior components of the electro-stimulation device and may be exposed at the surface of the body of the electro-stimulation device through appropriately defined orifices in the device body. It is preferred that the electro-conductive elements are preformed and are not formed as part of the interior components but are capable of being attached thereto or to conductive elements in communication with the interior components. The electro-conductive elements may be made of a bio-compatible conductive material such as:—stainless steel, conductive rubber, conductive plastic, sputtered plastic or electro plated plastic etc. Suitable examples of electrode material are conductive styrene butadiene styrene (SBS) materials; the conductivity being imparted by carbon filer. The conductive SBS electrodes may be manufactured by injection moulding or extrusion. In one embodiment the preferred electrode material is conductive ethylene vinyl acetate (EVA); this material helps to reduce stiction between the device and the applicator when used. Another suitable material is conductive silicone rubber. The size and shape of the electro-conductive elements may be such that they cover or are exposed at most of the exterior surface of the device body. They may be of any shape or size save that there is a need for enough space between the elements to prevent shorting of the device. In one embodiment the electro-conductive elements are approximately rectangular in shape and are of approximate dimensions of 28 mm×13 mm. In this embodiment they are located at or upon opposite surfaces of the electro-stimulation device approximately 180 degrees apart. The purpose of these electro-conductive elements is to conduct a waveform from the electro-stimulation device to the musculature of the pelvic floor complex. In one preferable embodiment the electro-conductive elements are in plate form. In a further embodiment the electro-conductive elements may be annular in which case there are two annular electro-conductive elements forming two continuous bands around a circumference of the electro-stimulation device; preferably this is the circumference that is perpendicular to the axis of insertion. The electro-conductive elements may be manufactured from material that may deform in co-operation with the deformation of the device body. In an alternative embodiment the electro-conductive elements may be located on resiliently deformable arms that communicate with the interior of the device and which are compressed as the electro-stimulation device is compressed. The electro-conductive elements may be sprung to maintain correct pressure on the wall of the vaginal or anal endocavity during use. In a further embodiment the electro-conductive elements comprise a clipping mechanism that enables the conductive elements e.g. wiring, inside the device to be clipped to the electro-conductive elements and thereby electrically connect them to the PCB. In one embodiment the conductive element is integrally moulded with the electro-conductive elements.

In a preferred embodiment all of the electrical components of the electronic sub-assembly apart from the electro-conductive elements and associated wiring but including the activation mechanism are enclosed in whole or in part within a chassis. The interior of the chassis is able to accommodate the PCB and through appropriately located orifices is able to allow the conductive paths to pass from the device body into the chassis to make electrical contact with the PCB. Preferably at one end of the chassis there is an opening which may accommodate the activation means for the device. The activation mechanism may be partly enclosed within the chassis. In a preferred embodiment the chassis comprises two components that reversibly engage with each other to provide an enclosed section of the chassis and providing an open section of the chassis. The PCB is preferably located within the enclosed section and the activation means is associated with both the closed and open sections. The activation means will be described more fully below. The benefit of the enclosed section of the chassis is that it is able to protect the sensitive components of the PCB during manufacture of the device or its use and from ingress of liquid. It has the further advantage of preventing or limiting egress of material from the components within the chassis. Preferably the chassis is manufactured from polypropylene or ABS (acrylonitrile butadiene styrene) polymers. During manufacture of the device the chassis comprising the PCB and activation mechanism may easily be inserted and bonded into a pre-moulded cavity within the moulded device body. This cavity being in communication with other smaller cavities that accommodate the surface exposed electro-conductive elements and their conductive paths such as wiring. This arrangement provides an easy means for assembly of the device from the individual components to provide a robust device.

Thus in a further embodiment the present invention provides an electro-stimulation device for the electro-stimulation of the musculature of the pelvic floor complex e.g. for the treatment of anterior and posterior pelvic floor muscle dysfunction, comprising a device body and at least two electro-conductive elements, located at the device surface, and anchored to and resiliently biased against a point located within the interior of the device such that the electro-conductive element may be reversibly compressed towards the interior of the device. In a preferred embodiment at least one of the electro-conductive elements is part of a device assembly as hereinafter described. Preferably at least one of the electro-conductive elements is anchored to an interior point of the device via an arcuate arm member made of resiliently deformable material.

In use the device of the present invention will be operated on deployment by the user to provide a pre-defined waveform of electrical pulses that are used to provide the neuromuscular electro-stimulation of the musculature of the pelvic floor complex. The waveform characteristics of the electrical stimulation signal are not alterable by the user e.g. patient, the waveform being pre-determined and pre-programmed in a microprocessor located on the PCB within the device.

The microprocessor controlled circuitry is pre-programmed to provide the desired waveform before assembly of the electro-stimulation device. Suitable waveforms that may be used are as described in WO 97/47357 or U.S. Pat. No. 6,865,423, the disclosures of which are hereby incorporated in their entirety by reference. Thus in one embodiment the waveform may comprise two or more components each component being a train of regularly spaced pulses. In one embodiment a second component is combined with the first component but the second component has spacing between successive pulses that is less than the spacing between successive pulses in the first component. In a further embodiment there is a third component that has spacing between successive pulses that is less than the spacing between successive pulses in the second component. In a further embodiment there may be periods of relaxation between sets of pulse trains. In this embodiment it is preferred that the period of relaxation is at least equal to the period of stimulation. The treatment cycle may be over a total period of three hours or less, preferably 2 hours or less, preferably 1 hour or less, and most preferably less than 1 hour. In a particularly preferred embodiment the period for the treatment cycle is 45 minutes or less. The treatment will typically be delivered through a combination of stimulation and rest periods. Each combination is typically 2 minutes or less, preferably 1 minute or less. In one embodiment the stimulation phase is of the order of 10 seconds and the recovery phase is of the order of 50 seconds. In a preferred embodiment the recovery phase is of the same order or greater than that of the stimulation phase and preferably both phases are of the order of 5 to 10 seconds. The first component may have a pulse repetition frequency between 1 and 15 Hz, more preferably between 1 and 6 Hz or between 5 and 15 Hz. The second component may have a pulse repetition frequency between 30 and 60 Hz, more preferably between 40 and 60 Hz. The third component may have a pulse repetition frequency between 80 and 300 Hz, more preferably between 80 and 200 Hz. The pulses may have a pulse width of 50 to 350 microseconds. The pulse width for each component may be of the same magnitude or may be different for each component. The pulse width may be narrow during the early stages of the treatment cycle and then increased gradually or in steps throughout the treatment cycle. Variation of the pulse width in this way may be used as an alternative to pulse amplitude variation or in addition to pulse amplitude variation during the treatment cycle. The amplitude of the pulses for each component may be of the same magnitude or may be different for each component. The pulse amplitude for each component may be of a fixed magnitude throughout the treatment cycle or preferably may be set at one or more magnitudes at one or more periods in the treatment cycle. The pulses may be between 0 and 90 mA. In one preferred embodiment, the pulse amplitude is set at a low level initially and is ramped up through the treatment cycle to a higher amplitude. In a preferred embodiment the waveform consists of a series of pulses of approximately 150 to 350 microseconds at a maximum voltage of 60 volts. The electro-stimulation device is programmed to adjust the output level of the device automatically over a period of time from zero volts up to the treatment maximum over a period of approximately 45 minutes. This will ensure a safe comfortable start for the treatment cycle and enables comfortable attainment of the maximum output by using the initial accommodation to the lower intensity pulses. The current is preferably applied, regulated and increased through the treatment period of around 20 to 50 minutes, preferably 20 to 45 minutes, more preferably 20 to 40 minutes. Treatment is preferably started at less than 45 mA, more preferably less than 40 mA and rises to 40 mA or more, preferably 45 mA or more for the last ten minutes of the treatment with a series of ramps in between. In one embodiment based on a pulse frequency of 35 Hz and a pulse width of 250 microseconds for example, the current is applied at 6 mA after insertion and rises to 12 mA over the first 10 minutes. Then the current is ramped from 12 mA to 40 mA over the next 10 minutes. Then the current is held at 40 mA over the next 10 to 15 minutes. Thus, the profile commences with a low impact on the user and then increases in intensity during the 30-45 minute treatment cycle. This cycle has been found to be particularly useful for use in the electro-stimulation devices of the present invention.

It is also envisaged that in accordance with the present invention the electro-stimulation devices with or without applicators may be provided as a pack of devices offering a complete series of, for example, daily treatments for incontinence. In one embodiment it is envisaged that the pack may comprise electro-stimulation devices that have different treatment waveforms. In this situation the devices may be used in sequence providing increasingly more intense treatment regimes as the user proceeds through the course of a complete treatment.

The present invention further provides for a method of treatment of anterior and posterior pelvic floor muscle dysfunction, which method comprises use of an electro-stimulation device according to the present invention. In a preferred embodiment the method comprises use of the device for the treatment of anterior and posterior pelvic floor muscle dysfunction according to the invention, which utilizes an applicator.

It is envisaged that the electro-stimulation device of the present invention may be used in circumstances where there is no recognized dysfunction of the musculature of the pelvic floor complex that has resulted in any symptoms of dysfunction e.g. incontinence. In these circumstances the devices of the present invention may be used to improve the performance of the musculature of the pelvic floor complex prior to dysfunction or to assist in preventing dysfunction. As an example women may use the device in advance of pregnancy to strengthen the musculature of the pelvic floor or to ensure it is in good physical condition prior to pregnancy and child birth.

In one embodiment, the electro-stimulation device comprises a removable tab or string attached to the device, which assists with removal of the device. This tab or string may also act in co-operation with the internal components of the device to activate or de-activate the device in-situ. The string being in the form of a pull-string with a mechanism that acts upon the internal components e.g. battery under applied force/torque to the string. In this embodiment, the device may be placed in-situ through use of the applicator and the string is then pulled gently to activate the device.

In a preferred embodiment, the microprocessor-controlled circuitry incorporates a delay after activation to ensure that the electro-conductive element surfaces are in place before the treatment cycle commences. In further embodiments, the electro-stimulation device may comprise one time activation/deactivation mechanisms associated with the internal components. Examples of such mechanisms include: means for detecting a change in the impedance of the electro-conductive elements after insertion of the device; use of gel shorting electro-conductive elements; zinc/air battery activation; use of light sensors to detect insertion; pressure sensors detecting expansion of the device on deployment and compression of the device during removal; relay switch in base activated by applicator; Hall effect switch in base activated by applicator; removal of a thin plastic isolator by applicator to make contact with battery; activation via expulsion from the applicator e.g. use of reed switch and magnet; and initial additional compression of the device on expulsion from the applicator acts on a pressure switch.

In a preferred embodiment, the device comprises an activation mechanism associated with the internal circuitry of the device and which is activated through force applied to the activation mechanism via the inner member of the applicator, which is exterior to the device. In this embodiment the activation mechanism comprises a switch component which is associated with both the microprocessor controlled circuitry located within the device body and is also capable of being contacted by the inner member of the applicator and further comprises at least two switch contacts associated with the circuit that may be brought into contact through interaction with the switch component to activate the circuit. In one embodiment, the movable switch component may be in the form of a jack plug arrangement and the switch contacts may be located within a jack socket arrangement within the device, the jack plug corresponding to the movable switch component. Movement of the switch component relative to the device body forces the plug of the switch component into the socket incorporating the two switch contacts forcing them into contact and thereby activating the circuit.

In a preferred embodiment the movable switch component, whilst being exposed to the exterior of the device, is held captive with the related internal components of the switch in the device. This means that the movable switch component whilst being capable of movement relative to the device body cannot in its entirety be removed from the device body. The captive nature of this switch component within the device is important for enabling effective deactivation of the device. In a preferred embodiment, the movable switch component further comprises a cord located upon or attached to an exterior surface of the component. Use of this cord enables deactivation of the device before the device is removed from the patient. When the device is in-situ and activated the cord passes from the device and out of the patient where it can easily be accessed by the patient. When the patient desires to deactivate and remove the device the patient pulls on the cord. The pulling force applied to the cord is transferred to the movable switch component, which under this applied force is forced away from the two switch contacts breaking the circuit. As the movable switch component is captive within the device there comes a point where it is unable to move any further relative to the device body at which point the applied pulling force is applied to and impacts upon the whole device, which now may be removed under the continued application of the pulling force on the cord. The relative force required to move the switch component apart from the switch contacts is much less than that required to remove the device from the patient. Because of this relative imbalance in forces, the device is always deactivated early in the removal cycle ensuring comfortable removal of the device by the patent. In a further embodiment, the socket also comprises holding means to hold the plug in place within the socket. This holding means may take the form of low-pressure spring arrangements that contact the plug surface and clamp it in the engaged position. This holding means may also take the form of a detent arrangement. The force required to disengage the plug from these holding means is significantly less than the force required to remove the whole device from the patient under the action of pulling the cord.

In a preferred embodiment, the captive functionality is imparted by the interaction of one or more protrusions on the movable switch component with one or more slots within the chassis of the electronic sub-assembly. The slots are closed at one end to ensure that when the protrusions of the movable switch component are engaged with the slots on assembly the movable component is unable to be removed from engagement with the chassis. In one embodiment, the protrusions may take the form of resiliently deformable arms that are attached towards the distal end of the component and being aligned parallel to the line of insertion into the device with the ends of the arms being located to the proximate end of the component. The ends of the arms have outward facing barbs that extend beyond the external circumference of the movable component. During assembly when this movable component is inserted into the slotted section of the chassis, the barbed arms are forced inwards towards the centre line of the component such that the barb surfaces no longer extend beyond circumference of the movable component. On insertion the barbed arms are held in this position, until the closed slots are encountered at which point the barbed arms are able to move into the static position with the barbed ends engaged within the slots of the chassis. This arrangement allows deformation of the movable component on assembly whilst preventing removal after assembly. In a further embodiment it is envisaged that the chassis body may further comprise guide means for these barbed arms to aid assembly; these guide means may take the form of grooves located on the internal surface of the chassis body and which are in communication with the exterior of the chassis boy and the closed slots of the chassis.

Thus in a further embodiment the electro-stimulation device of the present invention may further comprise an activation mechanism comprising a movable switch component captive within the device and having at least one of its surfaces exposed to the exterior of the device, the activation mechanism being capable of activation through movement of the switch component by the applicator on expulsion of the device from the applicator. It is preferred that the switch component is exposed towards the distal end of the device. It is also preferred that the switch component is moved or activated by impact from the inner member of the applicator, most preferably by impact of the proximate end of the inner member on the distal surface of the switch component.

BRIEF DESCRIPTION OF THE DRAWINGS

For a better understanding of the invention, and to show how the same may be carried into effect, reference will now be made, by way of example, to various specific embodiments of the invention as shown in the accompanying diagrammatic drawings, in which:

FIG. 1 (b) (i) shows a cross-sectional view of the device perpendicular to the axis of insertion (x) of the device, 1 (b) (ii) shows a side view of the device and 1 (b) (iii) shows a top view of the device, FIGS. 2 (a) and (b) show in perspective view an electro-stimulation device according to the present invention in the non-compressed and compressed state, FIGS. 3 (a) and (b) show an applicator arrangement for use with the electro-stimulation device of the present invention, FIGS. 4 (a), (b) and (c) show the arrangement of the internal components and electro-conductive elements for use in a electro-stimulation device according to the present invention and the assembly of the electro-stimulation device, FIG. 5 shows a schematic representation of and a circuit diagram for an internal circuit for use in the electro-stimulation device of the present invention.

FIG. 10a shows in perspective view an electro-stimulation device according to the present invention; FIG. 10b shows the device of FIG. 10a in various elevations, FIG. 11b shows the electronic sub-assembly of the device of FIG. 10a, and FIGS. 12 (a), (b), and (c) show an applicator arrangement for use with the electro-stimulation devices of FIGS. 6 and 10a.

DETAILED DESCRIPTION OF THE PREFERRED EMBODIMENT

Figure 1A:
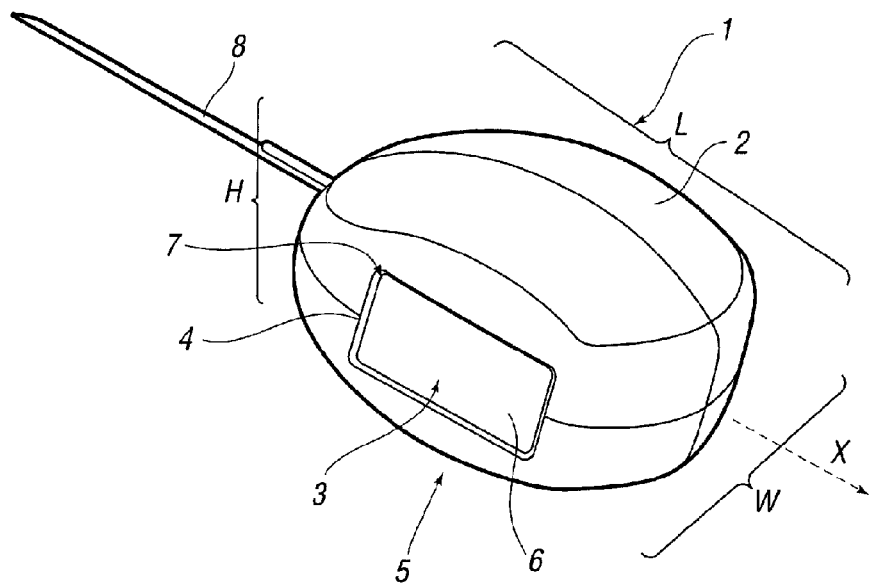
FIG. 1 (a) shows in perspective view an electro-stimulation device according to the present invention.
Figure 1B:
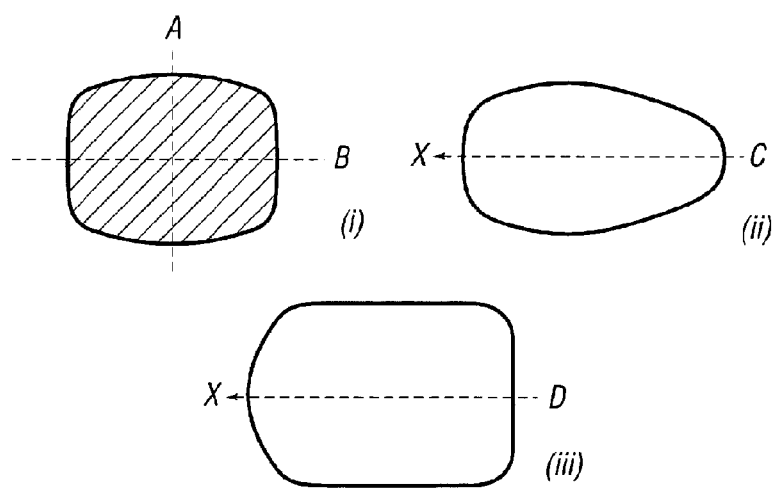

Referring to FIG. 1 (a) an electro-stimulation device (1) is shown in the non-compressed, fully expanded state. The device (1) has a body (2) which has been constructed from bio-compatible resiliently compressible foam. Electrode components hereinbefore and after also referred to as electro-conductive elements (3 and 3' not shown) emerge from within the body (2) of the device and are located at the surfaces (4 and 4' not shown) on sides (5 and 5' not shown) of the device (1). The electro-conductive elements (3 and 3' not shown) are relatively flat. In this particular embodiment the electrode components (3, 3') are in communication with the internal components (not shown) of the device (1) through internal conductive paths. They pass from within the device (1) to provide electrode surfaces (6 and 6' not shown) that are located in approximately the same plane as the surfaces (4, 4') of the sides (5, 5') of the device. The main body of the flat electrode components (3, 3') are located below the surface (4, 4') of the body (2) within a hollow cavity (not shown) within the body (2) of the device (1). The surfaces (6 and 6' not shown) of the electro-conductive elements (3, 3') appear through these openings (7 and 7' not shown) of the body (2). In one embodiment the electrode components (3, 3') may be surface mounted on the body (2) of the device (1); in this embodiment the surface mounted electrode components (3, 3') may be in contact with conductive paths that communicate with the interior of the body (2). The interior components of the device (1) are not shown in this Figure but are described in more detail below. The device (1) has a cord (8) which passes through a hole (not shown) in the body (2) of the device and communicates with and is attached to the interior components of the device (1). The cord (8) may be attached to interior components which enable the cord (8) to act upon the internal mechanisms of the device (1) in order to activate or deactivate the device (1) during use. The cord (8) may be made of string or similar materials, plastic materials or for example bio-compatible metal.

The dimensions of the device (1) which, in the non-compressed state, are such that the length (L) is greater than the width (w), which is in turn greater than the height (h). This device (1) is therefore an example of a device according to the invention where when viewed in cross-section along the axis of insertion (X) the device (1) has a non-uniform symmetrical cross-section with two planes of symmetry. This non-uniformity means that the device (1) is less prone to rotation or displacement relative to the axis of insertion (X) during use of the device (1). The device (1) has no sharp edges whilst having clearly defined surfaces that are connected to each other by gently curving regions. The compressible properties of the device (1) ensure resilient contact with the endocavity during use, its overall dimensions and shape, coupled with the smooth curvature of communicating surfaces, enables the device (1) to be easily and comfortably inserted during use, whilst at the same time limiting or preventing unwanted rotation and displacement during use. Referring to FIG. 1 (b) the cross-sectional shape of the device is shown in (i); the cross-section being perpendicular to the axis of insertion (x) of the device. Here it can be seen that the shape is broadly rectangular with softened rounded corners. The perpendicular cross-sectional shape exhibits two axes (A and B) of reflective symmetry and a single axis of rotational symmetry along the axis of insertion. Referring to FIG. 1 (b) the device is shown in side perspective in (ii); here it can be seen that in side profile the device has a single axis of reflective symmetry C, which is along the axis of insertion X of the device. In side profile there is no rotational axis of symmetry. Referring to FIG. 1 (b) the device is shown in top perspective in (iii); here it can be seen that in top profile the device has a single axis of reflective symmetry D, which lies along the axis of insertion X of the device. In top profile there is no rotational axis of symmetry.

Figure 2A:
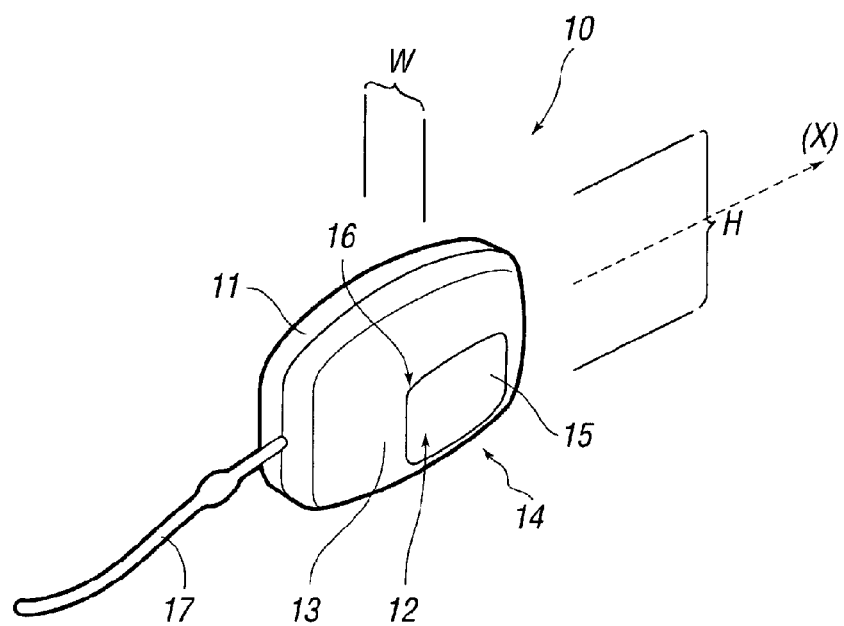
Figure 2B:
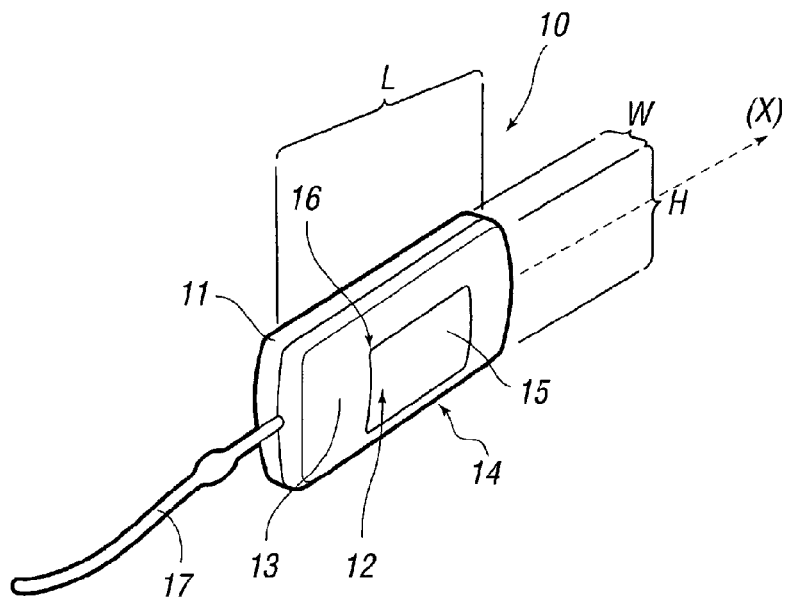

FIGS. 2 (a) and (b) show a device (10) whilst being broadly similar in construction to the device (1) illustrated in FIG. 1 has a more uniform cross-section and overall appearance. Thus the device (10) has a body (11), electrode components (12 and 12' not shown), body surfaces (13 and 13' not shown) on sides of the device (14 and 14' not shown), electrode surfaces (15 and 15' not shown), body openings (16 and 16' not shown) and a cord (17). FIG. 2(a) shows the device (10) in the non-compressed state. Here the device (10) has a width (W) which at its widest point is about 45 mm and has a height (H) which at its highest point is about 45 mm. The length (L) is about 60 mm. Thus the device (10) will have a relatively uniform cross-section at any point along the axis (X) of insertion. However, although the cross-sectional dimensions are approximately uniform the device (10), overall, has a shape which has distinct surfaces that are in communication with each other through smooth curves; this shape provides for a cross-section along the axis (X) of insertion that is non-circular. FIG. 2(b) shows the same device (10) as shown in FIG. 1 (a) but after it has been compressed. Here it is apparent that the length (L) of the device (10) has remained broadly unchanged at 60 mm but the height (H) has been reduced to 25 mm and the width (W) has been reduced to 15 mm. The compressed device has the overall appearance and dimensions of a Tampon. In this embodiment the device in compression is less than 20% of the volume of the device in the non-compressed state.

Figure 3A:
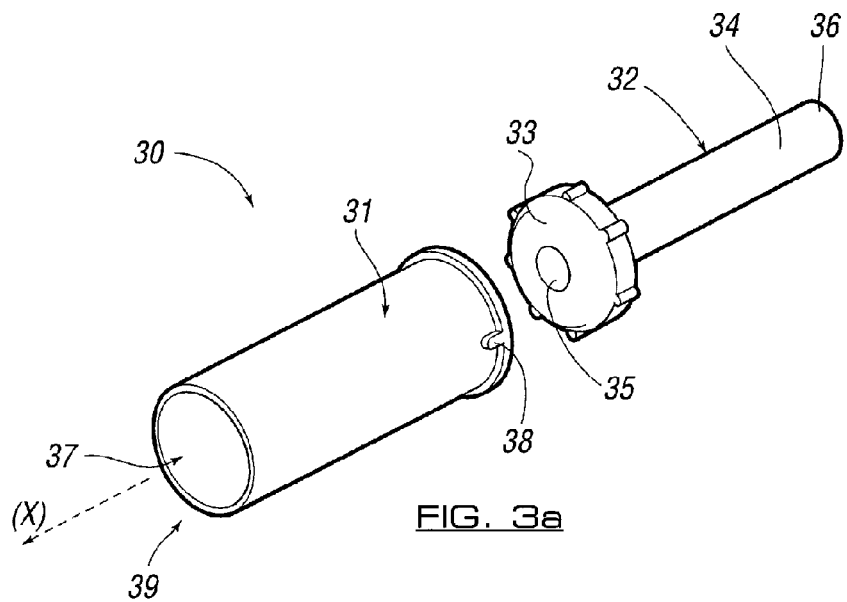
Figure 3B:
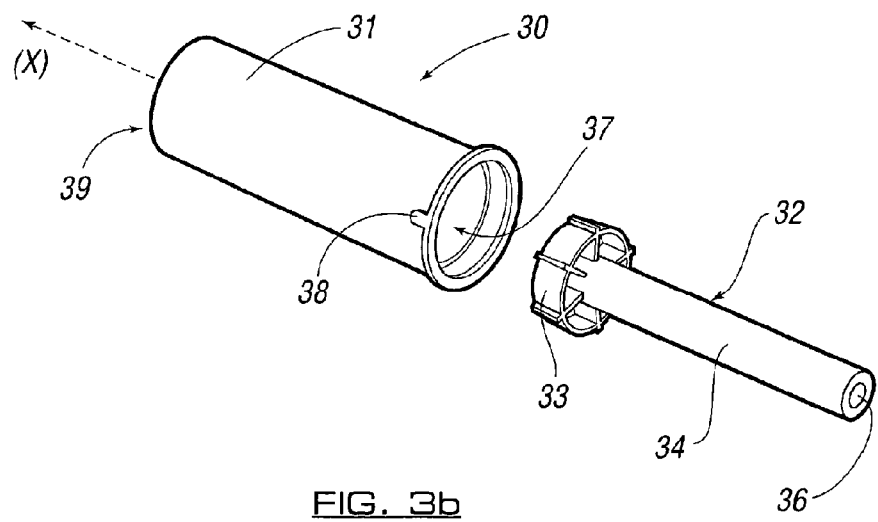

The device (10) in this compressed form is preferably inserted into the vagina or anus by means of an applicator. One suitable form of applicator is illustrated in FIG. 3. Referring to FIGS. 3 (a) and (b) there is shown an applicator (30) that has an outer member (31) and an inner member (32). The inner member (32) has a head (33) attached to a handle (34). The inner member (32) has a bore (35) that passes through the inner member (32) and opens at the end (36) of the handle (34). The inner member (32) is able to fit comfortably within the bore (37) of the outer member (31). The outer member (31) has a marker (38) that indicates the correct orientation for use of the applicator (30). When assembled the inner member (32) is located within the bore (37) of the outer member (31) and a compressed electro-stimulation device according to the present invention e.g. as illustrated in FIGS. 1 and 2 (a) and (b) is located within the bore (37) of the outer member (31) and adjacent the opening (39) of the outer member (31). When located within the bore (37) the compressed device is retained in the compressed state. The device is orientated within the applicator such that the cord of the device (not shown in this Figure) is able to pass along the bore (37) of the outer member (31) through the bore (35) of the inner member (32) and emerge from the end (36) of the inner member (32). Once assembled the applicator (30) with device are ready for use. In order to position the device in the vagina or anus of a user the outer member (31) of the applicator (30) is placed at the vaginal introitus (opening) or anal sphincter and then the inner member (32) is used to apply pressure to the end of the compressed device within the bore (37) of the outer member (32) and to force the device out of the bore (37) and into the endocavity of the vagina or anus. As the device leaves the bore (37) of the outer member (31) it is no longer held in compression and is able to expand and contact the walls of the vaginal or anal endocavity. The cord passes out of the vagina or anus and may be held and pulled by the user to remove the device from the vagina or anus once the treatment cycle is completed. In this embodiment the bore of the outer member will have a cross section on the axis of insertion (X) that is broadly similar in shape to the cross-section of the device when in the compressed state.

Figure 4A:
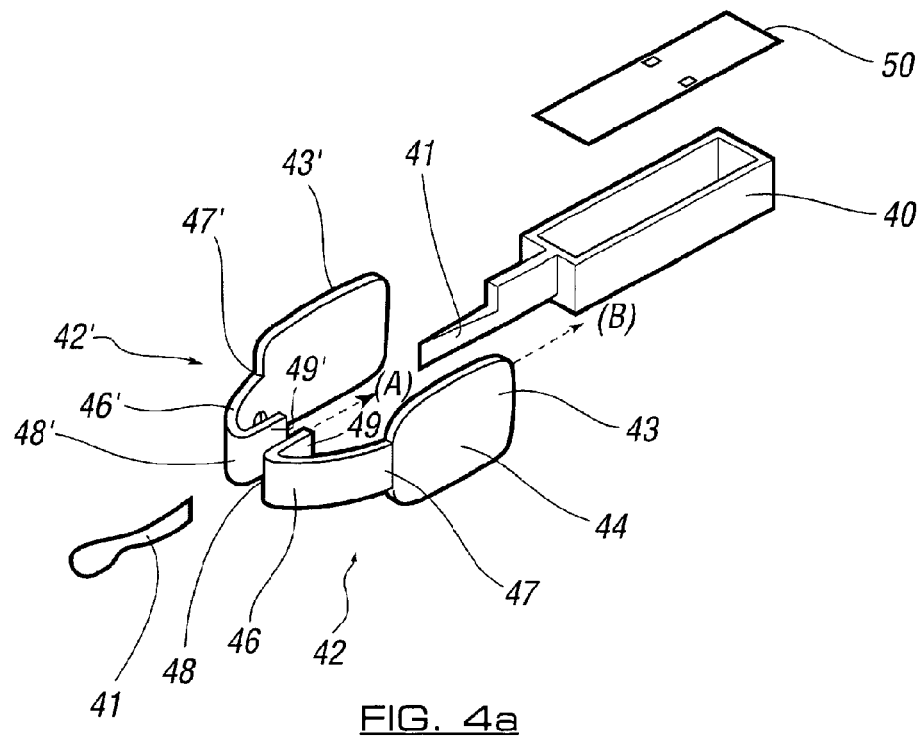
Figure 4B:
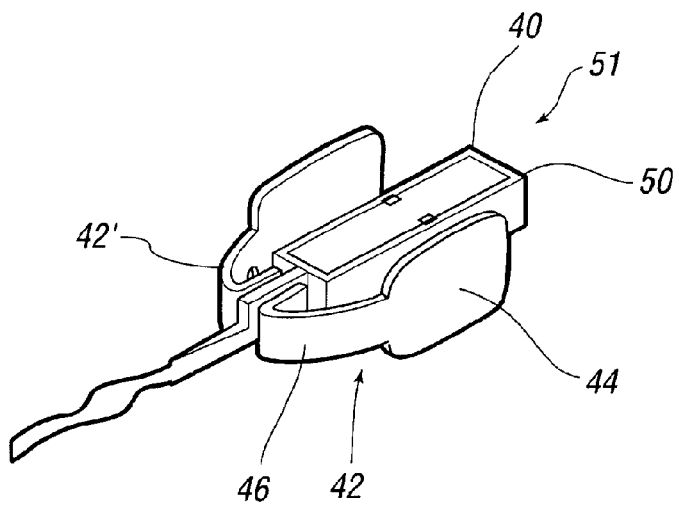

Referring to FIGS. 4 (a) (b) and (c) the inner components of the device of FIG. 2 are shown prior to assembly of the device. The inner components are housed in and/or connected with a chassis (40) that in this embodiment is injection moulded in unison with the string/cord (41) used to remove the device on completion of the treatment cycle. The electrode components (42, 42') have electrode pads (43, 43') that are broadly rectangular in shape. Each pad has an electrode surface (44 and 44' not shown) which is exposed on assembly of the device through openings (45 and 45' not shown) of the device body shell (53) as shown in FIG. 4(c). Each electrode component (42,42') has a resilient arcuate arm (46, 46') that at one end (47, 47') is connected to or formed with the pad (43, 43') and at the opposing end (48, 48') is connected to or formed with a flat plate section (49, 49') that is in a plane (A) which is approximately parallel to the plane (B) of the electrode pad (43,43'). In this embodiment the arcuate arms (46, 46') are connected to the pads (43, 43') at one of their narrower edges. The flat plates (49,49') may be attached to, or located within the chassis (40) as indicated in FIG. 4 (b), and in such an arrangement, that the electrode surfaces (44, 44') face away from each other and the chassis (40). In this arrangement the electrode components (42, 42') may be compressed and moved towards the chassis (40) by the application of pressure to the electrode pads (43, 43'). When the pressure is released the electrode components (42,42') return to their non-compressed state due to the spring like properties afforded to the components by the resilient deformable nature of the arcuate arms (46,46') and the nature of their attachment to and their spatial arrangement in relation to the chassis (40). A printed circuit board (50) is snap fitted into the chassis (40) and relevant contacts on the PCB are sprung connected against the ends of the electrode plates (49, 49'). In one embodiment the electrode components (42, 42') may be moulded as a single piece with the chassis (40) and the cord (41).

To assemble the electro-stimulation device the electrode components (42,42') are attached to the chassis (40) and the printed circuit board (50) is then snap fitted into the chassis (40) in sprung contact with the ends (49, 49') of the electrode plates. The power source (not shown) may be located on the printed circuit board (50) or may be located within the chassis (40) and connected to the printed circuit board (50). Once combined these components provide a unitary device assembly (51) shown in FIG. 4(b) that may then easily be used to manufacture the final device. The final device is assembled by taking the device assembly (51) and compressing the electrode components (42, 42') towards the chassis (40) so that the device assembly (51) is in the compressed state. In this state the device assembly (51) may then be inserted into a device body shell (53) manufactured from biocompatible materials such as a biocompatible foam or compressible material such as a thermoplastic elastomer. The device body shell (53) has a cavity (52) that is moulded so that it may accommodate the device assembly (51). The device body shell (53) has openings (45 and 45' not shown) through which the electrode pads (43,43') may be exposed to the exterior of the device once the device assembly (51) has been inserted into the cavity (52) of the device body shell (53) and the electrode components (42,42') are no longer under compression. Once the device assembly (51) has been inserted into the device body shell (53) then the shell may be welded closed along the open edges to the cavity and also welded around the openings (45,45') and electrode pads (44, 44'). In an alternative embodiment the device assembly (51) in the non-compressed state may be placed in a suitable mould and the device body (53) is then formed around the assembly (51) by injection moulding or a similar process. The components by their design and arrangement are easy to assemble and provide an easy to assemble compressible electro-stimulation device.

Referring to FIG. 5 there is shown an example of a circuit and a circuit block diagram that may be used in the device of the present invention. This circuit and the required components may be accommodated on a relatively small printed circuit board that may easily be accommodated within the body of the device. The circuit comprises a voltage generator, means for amplitude control, means for pulse switching and a logical control element (control logic pulse table).

Figure 6:
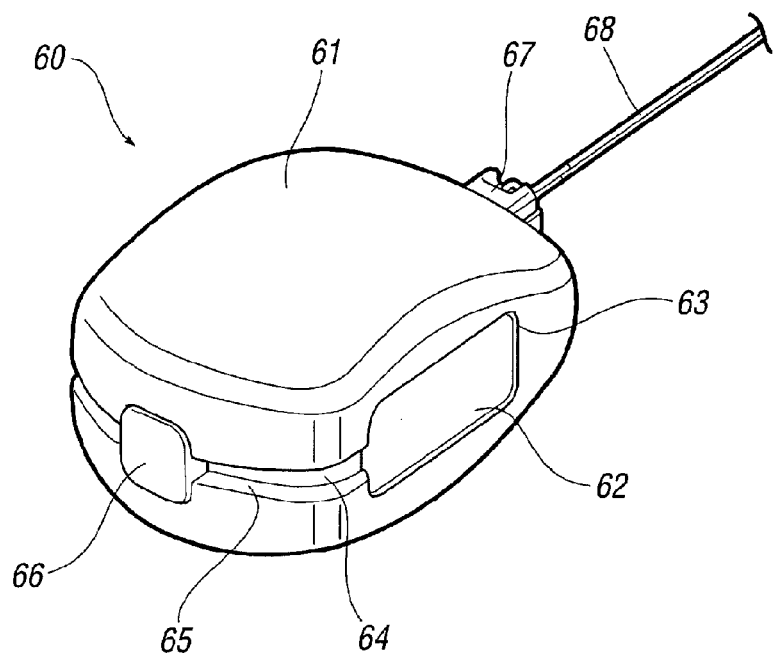
FIG. 6 shows in perspective view an electro-stimulation device according to the present invention.

Referring to FIG. 6 an electro-stimulation device (60) is shown in the non-compressed, fully expanded state. The device (60) has a body (61) which has been constructed from resiliently compressible polyurethane foam. The electro-conductive elements (62 and 62' not shown) are bonded to the surface of the body (61) of the device (60) with a suitable adhesive such as a cyanoacrylate based adhesive. The electro-conductive elements (62 and 62' not shown) are located within moulded recesses (63 and 63' not shown). Each electro-conductive element (62 and 62' not shown) has an arm section (64 and 64' not shown) which is located within arcuate recesses (65 and 65' not shown). The ends of the arm sections (not shown) are bent and pass into the interior of the body (61) of the device (60) towards the front of the device (60) to make contact with suitable connectors on the PCB (not shown) located within the interior of the device. In this embodiment the ends of the arms (not shown) are partly held in their location by the plug (66) located at the front of the device (60). The plug (66) also serves to protect the ends of the arms (not shown). Towards the rear of the device is located switch component (67) with a cord (68) attached thereto. The dimensions of this device (60) have the same relationships as discussed in detail for device (1) illustrated in FIGS. 1 and 1(a). In this embodiment the exposed surfaces of the arcuate arms are electrically insulated from the user by means of a suitable polymer film or mask applied to their surface and within the recess.

Figure 7:
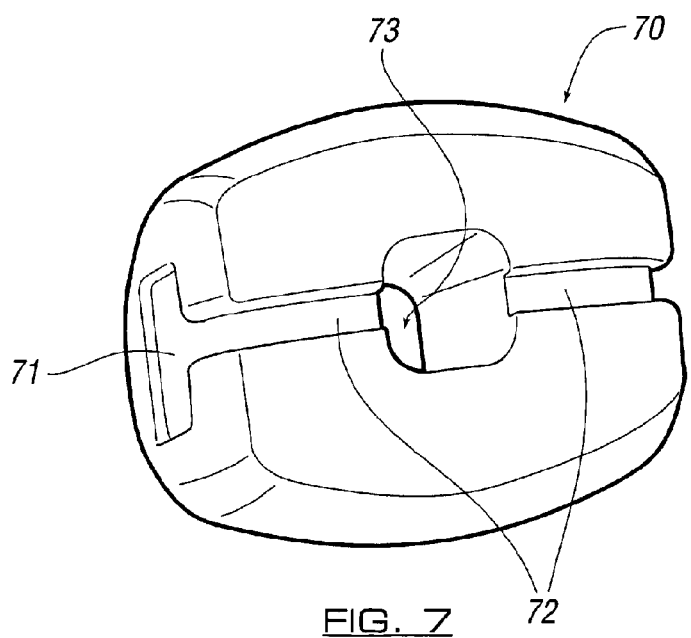
FIG. 7 shows in perspective view the device body of the electro-stimulation device of FIG. 6.

Referring to FIG. 7 a moulded electro-stimulation device body (70) is shown in the non-compressed, fully expanded state but without the internal components or electro-conductive elements. The moulded recesses (71) and (72) for the electro-conductive elements and their arms respectively can clearly be seen. Also show is the internal moulded cavity (73) which is for accommodating the internal electronic sub-assembly and switching mechanism (not shown). It can bee seen that the cavity passes through the moulded device body with openings at both ends.

Figure 8:
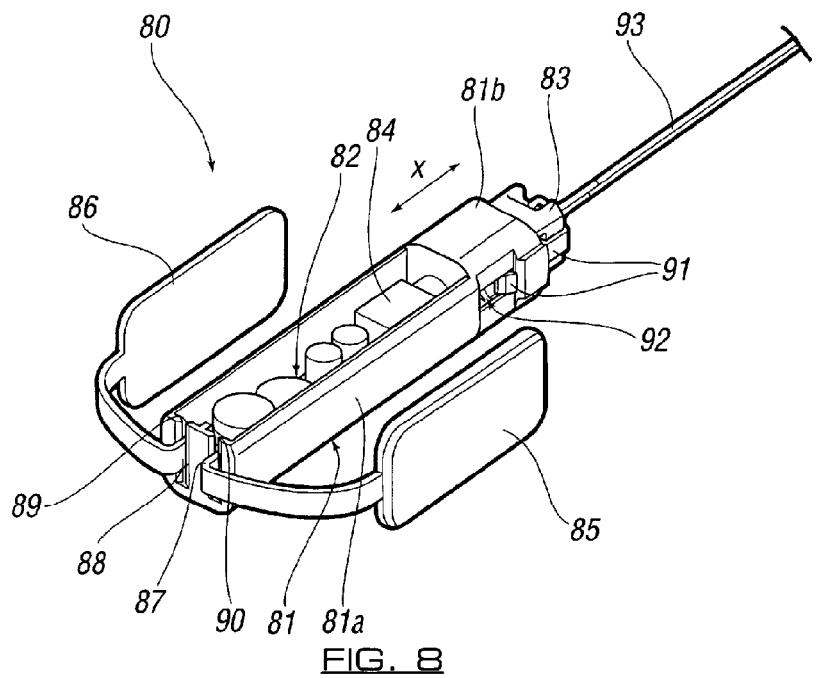
FIG. 8 shows in perspective view the electronic sub-assembly for the device shown in FIG. 6.

Referring to FIG. 8 the electronic sub-assembly (80) for the device of FIG. 6 is shown without the presence of the moulded device body. The electronic sub-assembly (80) consists of a chassis (81), a PCB (82), a switch mechanism consisting of a switch component (83) and a switch socket (84) with two switch contacts (not shown). The electro-conductive elements (85 and 86) have arm ends (87 and 88) that pass through openings (89 and 90) of the chassis (81) to make contact with terminals (not shown) on the PCB (82). The chassis (81) has two distinct regions (81a) and (81b). The switch component (83) is able to move relative to the assembly (80) in the direction indicated by double headed arrow X. The switch component (83) is captive within the end chassis component (81b). This is achieved by engaging the barbed arms (91) of the switch component (83) within the closed slots (92) of the end chassis component (81b). The barbed arms (91) are able to move freely in the directions indicated by X within the constraints of the closed slot (92). The plug end of the switch component (not shown) is able to engage with the switch contacts (not shown) of the switch socket (84). Also illustrated is the cord (93).

Figure 9:
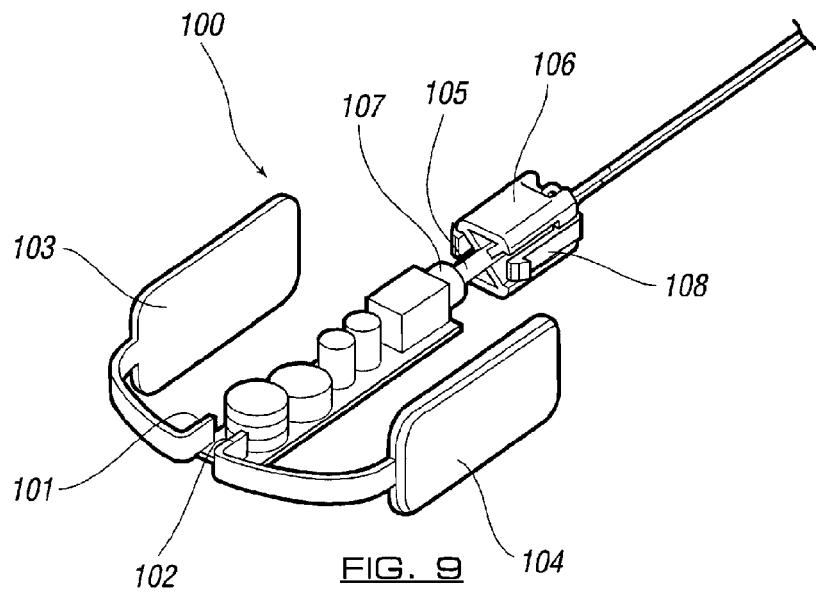
FIG. 9 shows in perspective view the electronic sub-assembly of FIG. 8 with the chassis removed.

Referring to FIG. 9 the electronic sub-assembly (100) for the device of FIG. 6 is shown without the presence of the moulded device body or the chassis as illustrated in FIG. 8. In this figure the spatial arrangement of the ends (101 and 102) of the electro-conductive elements (103 and 104) can clearly be seen. In addition without the chassis the plug end (105) of the switch component (106) can clearly be seen engaged within the socket of the switch socket (107). Also clearly exposed is one of the barbed arms (108) of the switch component (106). The other components are as described in FIG. 8.

Referring to FIGS. 10a and 10b an electro-stimulation device (200) is shown in the non-compressed, fully expanded state. The device (200) has a body (201) which has been constructed from injection moulded resiliently compressible polyurethane foam. The electro-conductive elements (202 and 202' not shown) are bonded to the surface of the device body (201) with a suitable adhesive such as a cyanoacrylate based adhesive. The electro-conductive elements (202 and 202' not shown) are located within moulded recesses (203 and 203' not shown). Each electro-conductive element (202 and 202' not shown) is connected to the internal PCB (not shown) through wire connectors (not shown) that are attached to clips (not shown) on the back of the electro-conductive elements (202 and 202' not shown). Towards the rear of the device is located switch component (204) with a cord (205) attached thereto. The device body also comprises recesses (206, 207, 208 and 209) in the body surface. The recesses may aid compressibility of the device. FIG. 10a illustrates the relative proportions of the device viewed from the side, top and back of the device. The dimensions of this device (200) have the same relationships as discussed in detail for device (1) illustrated in FIGS. 1 and 1(a).

Figure 11A:
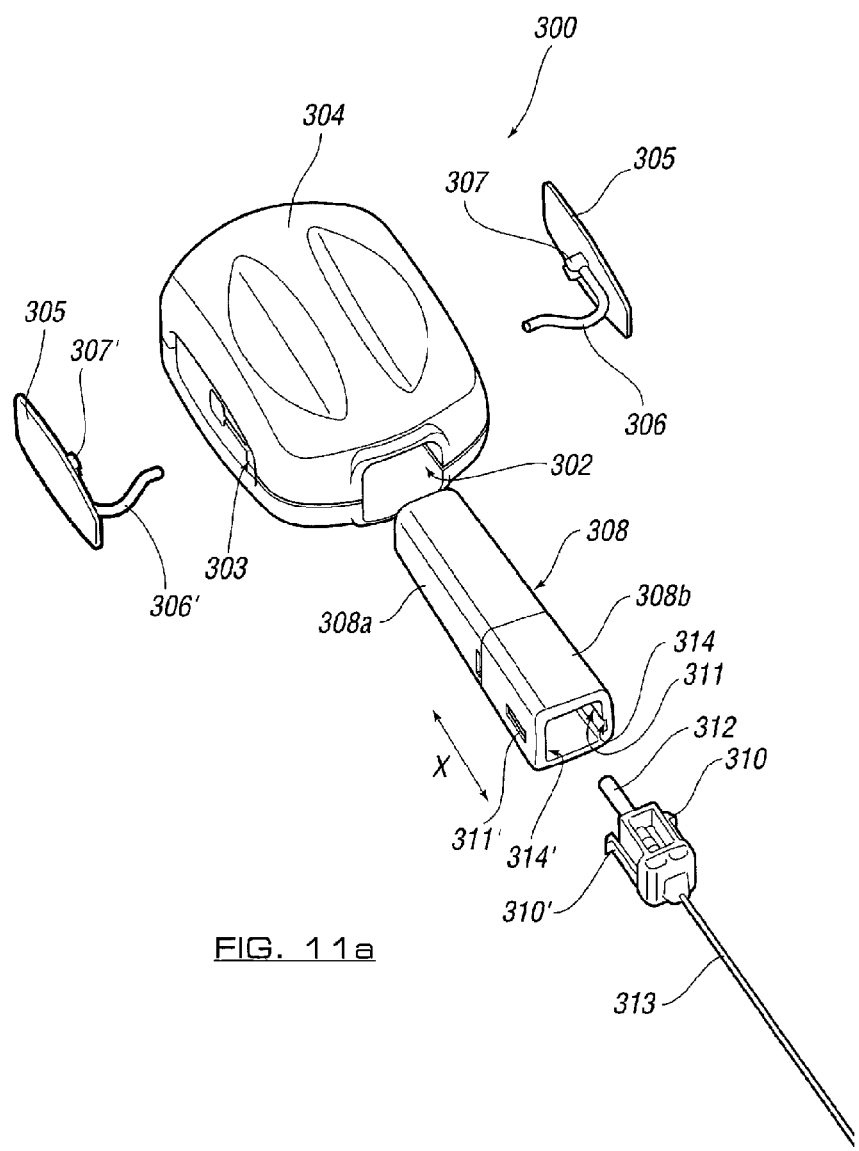
FIG. 11a shows in an exploded perspective view of the components of the device of FIG. 10a prior to its assembly.
Figure 11B:
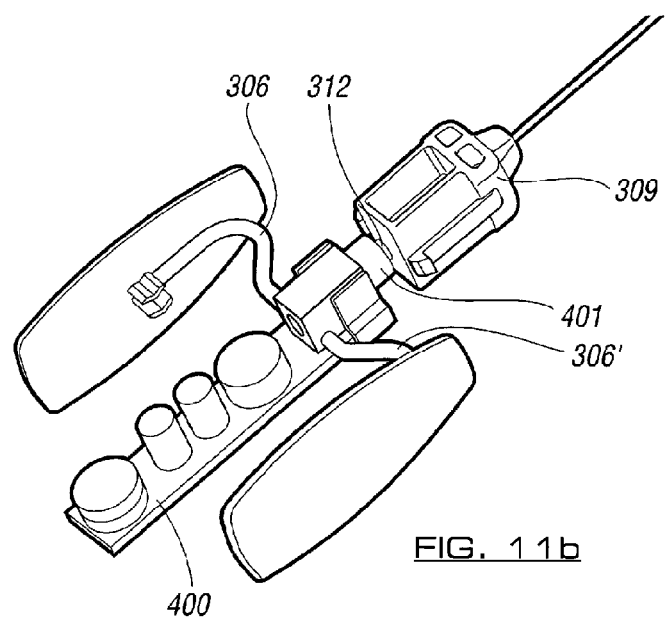

Referring to FIGS. 11a is the electro-stimulation device of FIGS. 10a and 10b showing in an expanded view the key components of the device (300) prior to assembly. Unlike the device illustrated in FIGS. 6 to 9, the device (300) is configured to be assembled through openings towards the rear (302) and sides (303 and 303' not shown) of the device body (304). Unlike the embodiment of FIG. 6 the opening (302) does not pass through to an opening towards the front of the device (300. The electro-conductive elements (305 and 305') are clearly shown with conductive wires (306 and 306') clipped to the back of each electro-conductive elements (305 and 305') via clips (307 and 307'). During assembly the conductive wires (306 and 306') pass through openings (303 and 303' not shown) to be connected to the PCB components within fully enclosed chassis (308), which is in two parts (308a) and (308b) that may be bonded or snap fitted to each other. The PCB components (not shown) are located within the front chassis component (308a). The switch component (309) shown here prior to insertion into the end chassis component (308b) is able to move relative to that component in the direction indicated by double headed arrow X. The switch component (309) once inserted is captive within the end chassis component (308b). This is achieved by engaging the barbed arms (310 and 310') of the switch component (309) within the closed slots (311 and 311') of the end chassis component (308b). The barbed arms (310 and 310') are able to move freely in the directions indicated by X within the constraints of the closed slot (311 and 311'). Also illustrated is the plug end (312) of the switch component (309), which is able to engage with the switch contacts (not shown) of the switch socket (not shown located within the chassis (308). Also illustrated is the cord (313). Also illustrated is guide means (314 and 314') located within the cavity of the end chassis component (308b), which engages with the barbed arms (310 and 310') of the switch component (310) during assembly to aid engagement of those arms with the closed slots (311 and 311'). The electro-conductive elements (305 and 305') and the chassis (308) are bonded in place and to the surface of the device body (304) with a suitable adhesive such as a cyanoacrylate based adhesive. The electro-conductive elements (305 and 305') are manufactured from conductive SBS or EVA and are located and bonded within moulded recesses (315 and 315' not shown). FIG. 11b illustrates the spatial relationship of the key components of the electronic sub-assembly after assembly of the device as illustrated in FIG. 11a but with the omission of the device body and chassis for clarity. The description for the numerically indicated components in FIG. 11b is the same as that used for like numbered components of FIG. 11a. FIG. 11b shows the PCB (400) and the point contact of the conductive wires (306 and 306') with the PCB (400). The figure shows the plug end (312) of the switch component (309), engaged with the switch contacts (not shown) of the switch socket (401).

Figure 12A:
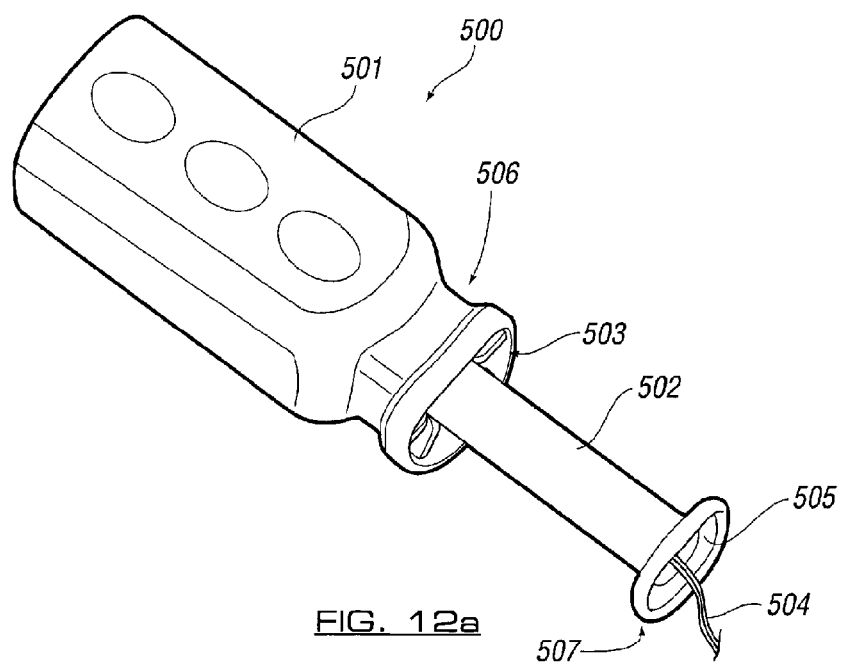
Figure 12B:
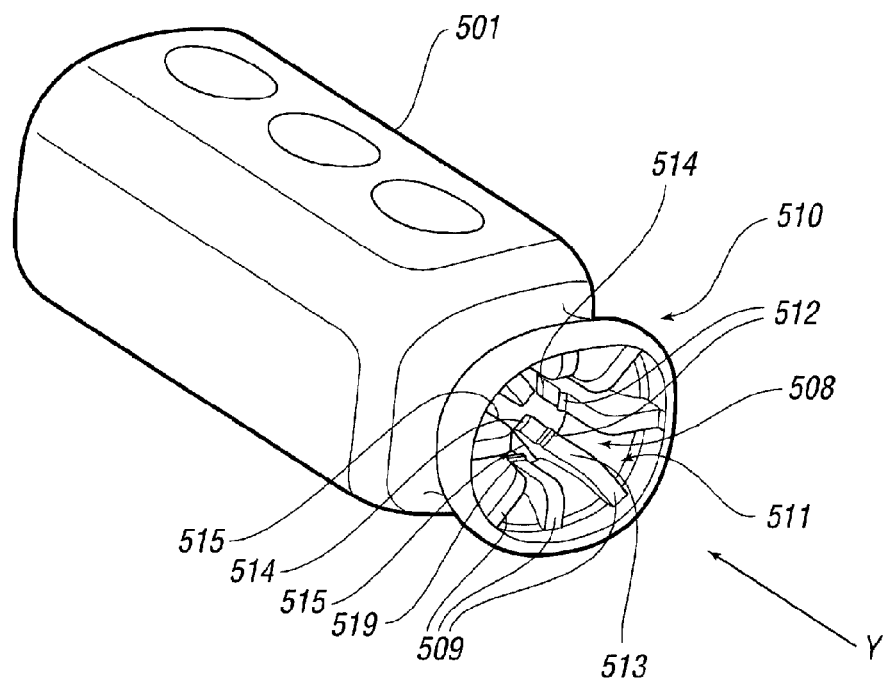
Figure 12C:
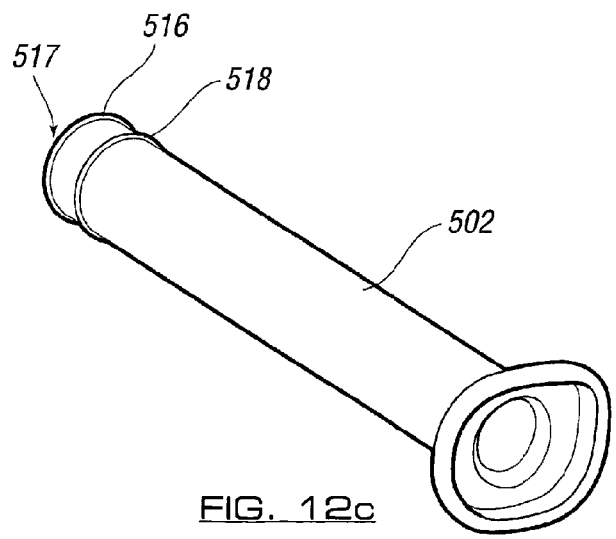

The devices of FIGS. 6 to 11 in their compressed forms are preferably inserted into the vagina or anus by means of an applicator. In both of these devices the activation mechanism is designed to be activated with the aid of the applicator during deployment of the device. One suitable form of applicator for this purpose is illustrated in FIGS. 12a to 12c. Referring to FIG. 12a there is shown an applicator (500) that has an outer member (501) and an inner member (502). The inner member (502) takes the form of a hollow cylinder which is engaged with the distal end (503) of the outer member (501). The applicator in this state has an electro-stimulation device (not shown) within the bore (not shown) of the outer member (501). The switch component (not shown) of the device will be aligned with the head (not shown) of the inner member (502) and is either proximate to the head of the inner member (502) or in contact engagement with the head of the inner member (502). In this state the device and applicator (500) are ready for use. The cord (504) of the device is shown passing through the bore of the inner member (502) and exiting through the bore opening (505) of the inner member (501). The outer member (501) has a gripping region (506) that is shaped to aid holding and actuation of the applicator (500) by the human hand. The inner member (502) has a flanged end (507) that presents a larger surface area to aid application of pressure by a human hand to the inner member (502) during use of the applicator (500). This applicator (500) is operated in a similar fashion to that described in FIGS. 3a and 3b. With reference to FIG. 12b the outer member (501) is shown without the inner member (502). This figure clearly shows the detent mechanism (508) which is exposed towards rear of the member (501). This detent mechanism (508) consists of a series of spaced apart fins (509) each attached at the distal end (510) of the outer member on its interior radial surface (511). The fins (509) protrude towards the central axis (Y) of the outer member (501). Each of the fins (509) has a ridge (512) on their inner surface (513) which, in this embodiment, is aligned with the ridges (512) on each neighbouring fin (509). In addition there is a chamfer surface (514) provided at the junction of the proximate edge (515) of each fin and their inner surface (513). This fin (509), ridge (512) and chamfer surface (514) arrangement provides a detent mechanism with corresponding features on the inner member (502) and a narrow bore within the outer member (510) to accommodate, secure and support the inner member (502) within the outer member (501) once the applicator (500) has been assembled. With reference to FIG. 12c the inner member (502) has an annular ridge (516) around its external circumference at its proximate end (517) and an annular notch (518) on the same surface and close to the annular ridge (516). The distance between the annular ridge (516) and annular notch (518) on the inner member (512) corresponds to the distance between the ridges (512) and chamfer surface (514) on each fin (509) of the outer member (501). Thus when the inner member (502) is inserted into the outer member (501) it is held in the correct axial position by the radial fin (509) arrangement and is securely held by the engagement of its notch (518) and ridge (516) with the corresponding ridge (512) and chamfer surface (514) of the outer member fins (509). In an alternative embodiment the radial notch (518) of the inner member (502) is replaced with a distal radial ridge. In this embodiment the distance between the proximate and radial ridges of the inner member (502) is just greater than the distance between the chamfer surface (514) and ridge (512) arrangement of the outer member (501). On assembly the proximate ridge (516) of the inner member (502) engages with the chamfer surface (514) and the distal radial ridge (518' not shown) impacts the frusto-conical surface (519) on the ridges (512) of the fins (509). For both embodiments on insertion of the inner member (502) into the outer member (502) these arrangements of ridges and notches engage with each other to provide the required detent effect.

All of the features disclosed in this specification for each and every embodiment (including any accompanying claims, abstract and drawings), and/or all of the steps of any method or process so disclosed, may be combined in any combination, except combinations where at least some of such features and/or steps are mutually exclusive.

What is claimed is:

1. A self-contained vaginal or anal electro-stimulation device, which device comprises a body being reversibly compressible in at least one dimension and at least two electro-conductive elements located at or on an external surface of the body, an internal power source and internal means for the generation and control of electrical pulses for the neuromuscular electro-stimulation of the musculature of the pelvic floor complex via the electro-conductive elements and wherein the device is conformable during its use and the control means are not alterable by a user of the device.

2. A device as claimed in claim 1 wherein the dimensions of the device in its non-compressed form are such that, when the device is in-situ in the desired location in the vagina or anus, the external surface of the device and the electro-conductive elements located at or on the surface of the device body are in contact with one or more surfaces of the vagina or anus.

3. The device of claim 1, wherein the body is manufactured from resiliently deformable/compressible material.

4. The device of claim 1, wherein the body is compressible due to a combination of the use of a resiliently deformable/compressible material for its manufacture and the nature of the device structure.

5. The device of claim 4, wherein the body is manufactured from resiliently deformable/compressible material and the interior of the electro-stimulation device body is hollow.

6. The device of claim 1, wherein the body of the device is moulded around the interior components of the electro-stimulation device to encapsulate them.

7. The device of claim 1, wherein the shape of the electro-stimulation device, when viewed in a cross-section taken perpendicular to the axis of insertion into the anus or vagina, is such that the electro-stimulation device is not freely rotated about that axis when in-situ.

8. The device of claim 7, wherein the shape of the electro-stimulation device when viewed in a cross-section taken perpendicular to the axis of insertion into the anus or vagina is non-circular.

9. The device of claim 1, wherein the electro-stimulation device is compressed to relative dimensions that are different in proportion to the dimensions of the device in the non-compressed state.

10. The device of claim 1, wherein the device has at least two dimensions perpendicular to the axis of insertion that have different degrees of compressibility.

11. The device of claim 1, wherein at least one of the dimensions of the electro-stimulation device perpendicular to the axis of insertion is may be reduced on compression by at least 20%.

12. The device of claim 1, wherein the volume of the device in the compressed state is reduced by at least 20% compared to that in the non-compressed state.

13. A device for the electro-stimulation of the musculature of the pelvic floor complex which comprises an electro-stimulation device according to claim 1 in combination with an applicator comprising an outer member and an inner member, the electro-stimulation device being located within the outer member.

14. The device of claim 1, wherein the output from the circuitry is a pre-defined waveform that is used to provide neuromuscular electro-stimulation of the musculature of the pelvic floor complex.

15. The device of claim 14, wherein the waveform characteristics of the electrical stimulation signal are not alterable by the user, the waveform being pre-determined and pre-programmed.

16. A method of stimulating the musculature of the pelvic floor complex, which method comprises providing electro-stimulation to the musculature of the pelvic floor complex using a device according to claim 1.

17. A method as claimed in claim 16 wherein the stimulation is for the treatment of anterior and posterior pelvic floor muscle dysfunction.

18. A method as claimed in claim 16, wherein the device is utilized with an applicator.

19. A device as claimed in claim 1 in which the circuitry incorporates a delay after activation to ensure that the electrode surfaces are in place before the treatment cycle commences.

20. A device as claimed in claim 1, wherein the electro-stimulation device comprises one-time activation/deactivation mechanisms associated with the internal components.

* * * * *

UNITED STATES PATENT AND TRADEMARK OFFICE
CERTIFICATE OF CORRECTION

PATENT NO. : 9,042,987 B2
APPLICATION NO. : 13/964825
DATED : May 26, 2015
INVENTOR(S) : Graham Peter Boyd et al.

It is certified that error appears in the above-identified patent and that said Letters Patent is hereby corrected as shown below:

Page 1 (item 71, Applicant) at line 1, Change "Middlesborough" to --Middlesbrough--.

Page 1 (item 73, Assignee) at line 1, Change "Middlesborough" to --Middlesbrough--.

In column 2 (page 1, item 56) at line 13, Under Other Publications, change "PCT/EP20006/011286." to --PCT/EP2006/011286.--.

In column 1 at line 59, Change "bulbospongiousus," to --bulbospongiosus,--.

In column 1 at line 59, Change "peroneii" to --peronei--.

In column 2 at line 42, Change "and or" to --and/or--.

In column 5 at line 43, Change "IDF" to --IFD--.

In column 7 at line 10, Change "and or" to --and/or--.

In column 15 at line 51, Change "removed." to --removed,--.

In column 19 at line 49, Change "bee" to --be--.

In column 20 at line 39, Change "FIGS. 11a" to --FIG. 11a--.

In column 23 at line 16 (approx.), In Claim 11, change "is may be" to --is--.

Signed and Sealed this
Twenty-eighth Day of June, 2016

Michelle K. Lee
*Director of the United States Patent and Trademark Office*